United States Patent
Tian et al.

(10) Patent No.: US 11,717,813 B2
(45) Date of Patent: Aug. 8, 2023

(54) ZEOLITE CATALYST FOR CATALYTIC CRACKING OF HYDROCARBONS TO PRODUCE PROPYLENE AND ITS PREPARATION AND USE

(71) Applicant: Henan University, Kaifeng (CN)

(72) Inventors: Yajie Tian, Kaifeng (CN); Xinyu He, Kaifeng (CN); Congzhen Qiao, Kaifeng (CN)

(73) Assignee: Henan University, Kaipeng (CN)

( * ) Notice: Subject to any disclaimer, the term of this patent is extended or adjusted under 35 U.S.C. 154(b) by 0 days.

(21) Appl. No.: 17/890,891

(22) Filed: Aug. 18, 2022

(65) Prior Publication Data

US 2023/0121156 A1 Apr. 20, 2023

(51) Int. Cl.
| | |
|---|---|
| *B01J 29/70* | (2006.01) |
| *B01J 37/04* | (2006.01) |
| *B01J 37/03* | (2006.01) |
| *B01J 37/02* | (2006.01) |
| *B01J 37/06* | (2006.01) |
| *B01J 37/30* | (2006.01) |
| *B01J 35/02* | (2006.01) |

(Continued)

(52) U.S. Cl.
CPC ............. *B01J 29/70* (2013.01); *B01J 35/026* (2013.01); *B01J 37/0236* (2013.01); *B01J 37/031* (2013.01); *B01J 37/04* (2013.01); *B01J 37/06* (2013.01); *B01J 37/08* (2013.01); *B01J 37/30* (2013.01); *C07C 4/06* (2013.01); *B01J 2229/20* (2013.01); *B01J 2229/38* (2013.01); *C07C 2529/70* (2013.01)

(58) Field of Classification Search
CPC ...... B01J 29/70; B01J 35/026; B01J 37/0236; B01J 37/031; B01J 37/04; B01J 37/06; B01J 37/08; B01J 37/30; B01J 2229/20; B01J 2229/38; C07C 4/06; C07C 2529/70
See application file for complete search history.

(56) References Cited

U.S. PATENT DOCUMENTS

| | | | | |
|---|---|---|---|---|
| 5,258,114 A | * | 11/1993 | Aufdembrink | ........ B01J 20/18 208/120.15 |
| 10,016,750 B1 | * | 7/2018 | Al-Khattaf | ............ C07C 11/04 |

(Continued)

OTHER PUBLICATIONS

Liu et al. ("Nature and Catalytic Role of Extraframework Aluminum in Faujasite Zeolite: A Theoretical Perspective", ACS Catal. 2015, 5, 7024-7033) (Year: 2015).*

*Primary Examiner* — Ali Z Fadhel
(74) *Attorney, Agent, or Firm* — Seed IP Law Group LLP

(57) ABSTRACT

A method for preparing a zeolite catalyst for catalytic cracking of hydrocarbons to produce propylene is provided, which specifically includes steps of mixing a silicon source, a templating agent, an aluminium source, and a solvent to form a zeolite precursor solution, which is then subjected to hydrothermal crystallization, washing, drying, and calcination to obtain a zeolite precursor; ion-exchanging the zeolite precursor with ammonium ions, followed by drying and calcination; and loading aluminum onto the ion-exchanged zeolite precursor as a carrier via incipient-wetness impregnation by using an aluminium-containing solution, followed by drying and calcination. Zeolite catalysts prepared by the method and use of the catalysts in catalytic cracking of hydrocarbons to produce propylene are also provided.

20 Claims, 12 Drawing Sheets

(51) Int. Cl.
    *C07C 4/06*         (2006.01)
    *B01J 37/08*      (2006.01)

(56) References Cited

U.S. PATENT DOCUMENTS

| | | | |
|---|---|---|---|
| 11,247,196 B2* | 2/2022 | Alsewdan | C01B 39/365 |
| 2004/0138051 A1* | 7/2004 | Shan | C01B 37/02 |
| | | | 423/700 |
| 2016/0221832 A1* | 8/2016 | Lai | B01J 20/28083 |
| 2017/0240431 A1* | 8/2017 | Burton | B01J 37/009 |
| 2019/0256365 A1* | 8/2019 | Burton | C07D 207/06 |
| 2019/0336954 A1* | 11/2019 | Wu | B01J 35/002 |
| 2020/0047168 A1* | 2/2020 | Hotta | F01N 3/08 |
| 2021/0162380 A1* | 6/2021 | Conant | B01J 29/047 |
| 2021/0214236 A1* | 7/2021 | Fu | C01B 39/205 |
| 2021/0339233 A1* | 11/2021 | Gao | B01J 20/28045 |
| 2021/0394165 A1* | 12/2021 | Gao | C01B 39/46 |
| 2022/0144725 A1* | 5/2022 | Podsiadlo | B01J 35/1061 |

* cited by examiner

ZEOLITE CATALYST FOR CATALYTIC CRACKING OF HYDROCARBONS TO PRODUCE PROPYLENE AND ITS PREPARATION AND USE

CROSS REFERENCE TO RELATED APPLICATION

This patent application claims the benefit and priority of Chinese Patent Application No. 202111202171.9, filed on Oct. 15, 2021, the disclosure of which is incorporated by reference herein in its entirety.

TECHNICAL FIELD

The present disclosure is related to the field of catalysts, and, in particular, to a molecular sieve or zeolite catalyst for catalytic cracking of hydrocarbons to produce propylene and its preparation and use, and, further to a ZSM-5 zeolite catalyst allowing for precise regulation of the Brønsted to Lewis acid molar ratio, which is useful in catalytic cracking of hydrocarbons to produce propylene.

BACKGROUND

In recent years, the wide use of polypropylene (PP) in the world has led to an increasing demand for propylene, which is the raw material for polypropylene production. Propylene is usually produced through naphtha steam cracking which, however, produces ethylene as a main product. The propylene supply is now far from meeting social demands. Moreover, the steam cracking process is generally carried out at high temperature (>750° C.), resulting in production of a large amount of carbon dioxide ($CO_2$) which is known as a greenhouse gas.

Studies have found that catalytic cracking processes using zeolites (such as ZSM-5, Beta and NaA zeolites) as a catalyst enable a reduced reaction temperature. Moreover, catalytic crackers can be reformed from existing steam crackers, thereby substantially reducing equipment investment. Therefore, catalytic cracking of hydrocarbons using zeolite catalysts to produce light olefins is more advantageous, also due to shape selectivity of the zeolites due to the pores and channels thereof and adjustable distribution of the acid sites in the zeolites. It has also been found that the zeolite catalysts can exhibit an increased propylene to ethylene molar ratio. The catalytic cracking route for production of propylene is thus undergoing rapid development. ZSM-5 zeolites, as a typical example of the zeolite catalysts, have attracted extensive attention due to their regular mesoporous structure and rich surface acid sites. During catalytic cracking of hydrocarbons including naphtha using ZSM-5 catalysts, the reactions typically proceed through a monomolecular mechanism, that is, the hydrocarbon molecules are bonded to surface acid centers in the ZSM-5 catalysts to generate carbocations, which then produce light olefins including ethylene and propylene by beta cleavage.

The acid centers or sites in ZSM-5 zeolites are mainly classified into Brønsted and Lewis acid sites. Current research has shown that initiation of the catalytic cracking of hydrocarbons is mainly related to the Brønsted acid sites and the Lewis acid sites play an important role in selective chain scissions of the hydrocarbons. It is generally considered that the Brønsted acid sites originate from H species bonded to the oxygen atoms in the Si-O-Al linkage in the ZSM-5 zeolite framework, and the Lewis acid sites originate from hydroxy groups bonded to the extra-framework aluminium (Al) atoms. Conventional hydrothermal synthesis of zeolites enables regulation of acidity of the zeolites through adjustment of the Al content in the synthesis solutions. An increase in the Al content (i.e., a decrease in Si to Al (Si/Al) molar ratio) in the zeolites leads to increasing acidity. Changes in acidity will influence conversion rates of the hydrocarbons and also bring remarkable effect on distribution of the products. Existing literature has shown that the strength of the acid sites in the zeolites can be effectively reduced by modifying the zeolites with transition metals or rare earth metals, which, although, leads to a decreased conversion rate of naphtha, causes secondary reactions of ethylene and propylene to slow down. In this case, the propylene yield can be increased by properly controlling the reaction conditions.

Even so, it is still difficult for the most commonly used ZSM-5 zeolites as a catalyst for the catalytic cracking of hydrocarbons to light olefins to realize a propylene to ethylene molar ratio of equal to 2 or higher. This is mainly because, at low pressure and high temperature at which the catalytic cracking of hydrocarbons is generally carried out, due to a carbocation mechanism the hydrocarbon molecules undergo beta cleavage which is not selective to propylene. Rather, the rate of reactivity of the carbon atoms present in the hydrocarbon molecules in the decreasing order is quaternary carbon>tertiary carbon>secondary carbon>primary carbon. For the hydrocarbons in naphtha, the number of secondary carbon atoms is the largest. Therefore, it tends to lead to high selectivity of ethylene and relatively low selectivity of propylene. It has been proven, that even if the cracking severity is suppressed by improving pore and acidity distribution of the zeolites, selectivities of both ethylene and propylene are increased, indicating that such zeolite catalysts are not selective only for propylene and the propylene to ethylene molarse ratio cannot be increased.

SUMMARY

Technical Problem

The global demand for polyolefins has boomed in recent years, leading to an increasing demand for propylene, which is the raw material for PP production. However, the propylene supply is now far from meeting social demands. Conventional steam cracking comes with disadvantages of low propylene yield, high energy consumption, and the like. Catalytic cracking can solve the problems existing in conventional steam cracking to a certain extent, but the products of the catalytic cracking still consist largely of ethylene due to the reaction mechanism and thus the yield of propylene is unable to meet the high demand therefor.

Low yield of propylene is mainly due to the difficulty of controllably modifying the distribution and strength of the acid sites in conventional zeolite catalysts. Taking as an example the ZSM-5 zeolites which are commonly used as a catalyst in the cracking of naphtha, it is desirable for the Brønsted to Lewis acid ratio to be precisely regulated, because this makes it possible to control the conversion of hydrocarbon molecules, which occurs at the surface acid sites, such that propylene is produced in high yield. However, although the total acid content of the zeolites can be varied simply by varying the Al content in the synthesis solutions, the Brønsted to Lewis acid ratio has already been determined when the Al concentration in the zeolites is determined during preparation thereof via hydrothermal synthesis. This fundamentally determines that the yield of ethylene is substantially higher than that of propylene. It has been reported that the distribution of the Brønsted and Lewis acid sites in the ZSM-5 zeolites can be regulated to a certain extent by modifying the zeolites with transition metals or rare earth metals. However, it is still difficult to increase the yield of propylene by precisely regulating the concentrations of the Brønsted and Lewis acid sites in the ZSM-5 zeolites so modified.

To solve the above problems, the present disclosure proposes to modify the ZSM-5 zeolites, the framework aluminium concentration of which has already been determined during preparation thereof, with aluminium by introducing a certain amount of extra-framework aluminium (EFAL) species into the zeolites via an incipient-wetness impregnation method. The amount of the EFAL species in the zeolites so modified can be precisely regulated. By varying the amount of the EFAL species introduced into the zeolites and forming extra-framework Al-OH groups in a quantitative manner, it is possible to controllably regulate the number of Brønsted acid sites in the zeolites and to produce higher yield of propylene from catalytic cracking of hydrocarbons. The present disclosure also provides a method for preparing such zeolite catalysts. The method is simple and easy to implement. Moreover, the starting materials used in the method are readily available industrially. Therefore, the method can be applied on an industrial scale.

Solution to Problem

The present disclosure provides a method for preparing a zeolite catalyst for catalytic cracking of hydrocarbons to produce propylene, the method comprising steps of:

(1) mixing a silicon source, a templating agent, an aluminium source, and a solvent to form a zeolite precursor solution, which is then subjected to hydrothermal crystallization, washing, drying, and calcination to obtain a zeolite precursor;

(2) ion-exchanging the zeolite precursor obtained in step (1) with ammonium ions ($NH_4^+$), followed by drying and calcination; and (3) loading aluminum onto the ion-exchanged zeolite precursor obtained in step (2), as a carrier, via incipient-wetness impregnation by using an aluminium-containing solution, followed by drying and calcination.

In an embodiment, the templating agent includes quaternary ammonium surfactants. Preferably, the quaternary ammonium surfactant includes tetrapropylammonium hydroxide (TPAOH) and/or tetrapropylammonium bromide.

In an embodiment, the aluminium source used in step (1) includes one or more of organoaluminum compounds, pseudo boehmite, alumina gel, and organic and inorganic acid salts containing aluminium as well as complexes and hydrates thereof.

In a further embodiment, the aluminium source includes one or more of pseudo boehmite, alumina, alumina gel, sodium aluminate, aluminium phosphate, aluminium chloride ($AlCl_3$), aluminum sulfate ($Al_2(SO_4)_3$), aluminium nitrate ($Al(NO_3)_3$), aluminium isopropoxide ($Al(OCH(CH_3)_2)_3$), and aluminium hydroxide.

In a yet further embodiment, the aluminium source includes one or more of $Al(NO_3)_3$, $Al_2(SO_4)_3$, $AlCl_3$, and $Al(OCH(CH_3)_2)_3$.

In an embodiment, the silicon source used in step (1) includes one or more of silica gel, fumed silica, inorganic silicates, organic silicates, white carbon black, and silicic acid. Preferably, the silicon source includes one or more of silica sol, tetraethyl orthosilicate (TEOS), and sodium silicate.

In an embodiment, the zeolite precursor solution obtained in step (1) contains $SiO_2$, the templating agent, $Al_2O_3$, and $H2O$ at a molar ratio of 100:(30-60):(0-4):(2000-6000).

In an embodiment, the hydrothermal crystallization is carried out at a temperature of from 130 to 170° C. for a period of time of from 2 to 15 days.

In an embodiment, in step (1), the calcination is carried out in air atmosphere at a temperature of from 300 to 650° C. for a period of time of from 4 to 12 hours.

In an embodiment, in step (2), the zeolite precursor obtained in step (1) is ion-exchanged with the ammonium ions at a temperature of from 20 to 120° C. for a period of time of from 2 to 48 hours.

In an embodiment, in step (2), the calcination is carried out in air atmosphere at a temperature of from 300 to 650° C. for a period of time of from 4 to 12 hours.

In an embodiment, in step (2), the ammonium ions are provided by an ammonium salt including one or more of ammonium chloride ($NH_4Cl$), ammonium nitrate ($NH_4NO_3$), and ammonium sulfate (($NH_4)_2SO_4$).

In an embodiment, the aluminum ions contained in the aluminium-containing solution used in step (3) are provided by an aluminum source including one or more of $Al(NO_3)_3$, $Al_2(SO_4)_3$, $AlCl_3$, and $Al(OCH(CH_3)_2)_3$, and are present in the solution at a concentration of from 0.1 to 10% by weight.

In an embodiment, in step (3), the incipient-wetness impregnation is carried out at a temperature of from 20 to 120° C. for a period of time of from 6 to 48 hours.

In an embodiment, in step (3), the calcination is carried out at a temperature of from 300 to 650° C. for a period of time of from 4 to 12 hours.

The present disclosure also provides a zeolite catalyst for catalytic cracking of hydrocarbons to produce propylene prepared by the method as described above.

In an embodiment, the zeolite catalyst has an MFI structure and has an average particle size of from 200 to 500 nm, and the zeolite catalyst has a Brønsted to Lewis acid ratio of from 0.1 to 1.

In an embodiment, the zeolite catalyst has a specific surface area of from 300 to 600 $m^2/g$, and a pore volume of from 0.3 to 0.7 $cm^3/g$.

The present disclosure further provides the use of the zeolite catalyst as described above in catalytic cracking of hydrocarbons to produce propylene.

The present disclosure also provides a catalytic cracking process for producing propylene from hydrocarbons by using the zeolite catalyst as described above as a catalyst.

Advantageous Effects

According to the method of the present disclosure, a certain amount of EFAL species is loaded onto the ZSM-5 zeolites via an incipient-wetness impregnation method. This can controllably regulate the Brønsted to Lewis acid ratio and thus control the conversion of the hydrocarbon molecules occurred at the acid sites such that propylene is produced in high yield. The increment in the number of the Lewis acid sites can be controlled by precisely controlling the amount of the EFAL species loaded onto the zeolites so that the Brønsted to Lewis acid ratio can be controlled. Further, the method is simple and easy to implement. Moreover, the starting materials used in the method are readily available industrially.

Figures 1A, 1B:
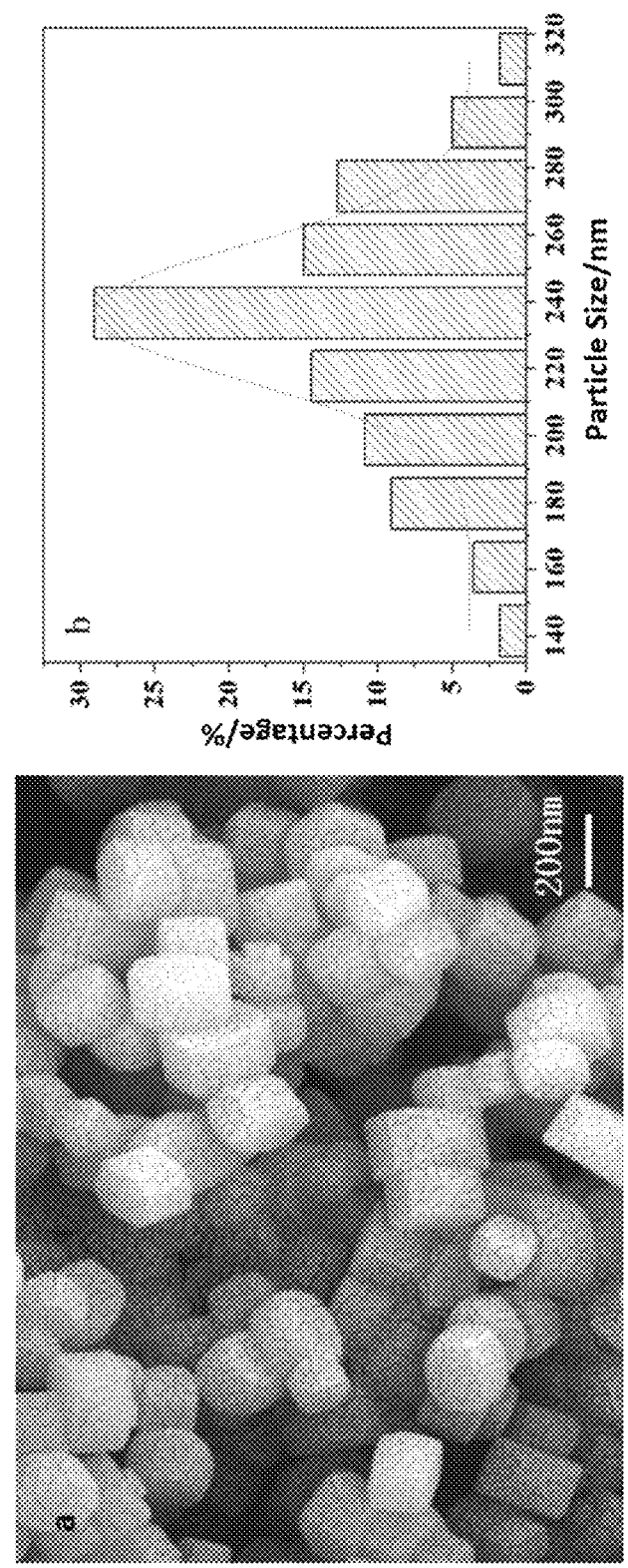
FIG. 1A-B shows (a) a scanning electron microscopy (SEM) image, and (b) particle size distribution, of a zeolite catalyst prepared in Comparative Example 1-1.

Table 1 shows silicon to aluminum molar ratios (Si/Al ratios) of the zeolite catalysts prepared in Comparative Examples 1-1 to 1-5, Examples 1-5, and Comparative Examples 2-2 and 2-3, determined by inductively coupled plasma atomic emission spectrometry (ICP-AES).

Table 2 shows concentrations of the Brønsted and Lewis acid sites in the zeolite catalysts prepared in Comparative Examples 1-1 to 1-5, Examples 1-5, and Comparative Examples 2-2 and 2-3, the Brønsted to Lewis acid ratio, and overall concentration of the acid sites (Brønsted and Lewis), measured by pyridine adsorption.

DETAILED DESCRIPTION

The following is a detailed description of the present disclosure, which describes the various embodiments and examples of the disclosure. However, these embodiments and examples are not intended to limit the present disclosure.

The range of values indicated by "from A to B" or "A to B" in this specification refers to a range including endpoint values A and B.

As used herein, the term "more" means a numerical value of 2 or greater.

As used herein, the term "may" shall mean performing the stated processes or operations or not performing the stated processes or operations.

All percentages are weight percent (wt %) unless otherwise specified.

As used herein, "room temperature" refers to a temperature within a range of from 10 to 40° C.

First Aspect

A first aspect of the present disclosure provides a method for preparing a zeolite catalyst for catalytic cracking of hydrocarbons to produce propylene, the method comprising: mixing a silicon source, a templating agent, an aluminium source, and a solvent to form a zeolite precursor solution, which is then subjected to hydrothermal crystallization; subjecting a product obtained from the hydrothermal crystallization to be washed with deionized water until neutral pH and then to be calcined to obtain a zeolite precursor; and ion-exchanging the zeolite precursor with ammonium ions, followed by drying and calcination.

The method according to the first aspect of the present disclosure further comprises loading aluminum onto the ion-exchanged zeolite obtained above, as a carrier, via incipient-wetness impregnation by using an aluminium-containing solution, followed by drying and calcination, to obtain the zeolite catalyst according to the present disclosure.

Zeolite Precursor Solution

The silicon source may include one or more of silica gel, fumed silica, inorganic silicates, organic silicates, white carbon black, and silicic acid. Preferably, the silicon source includes one or more of silica sol, TEOS, and sodium silicate.

The aluminium source may include one or more of organoaluminum compounds, pseudo boehmite, alumina gel, and organic and inorganic acid salts containing aluminium as well as complexes and hydrates thereof. Preferably, the aluminium source includes one or more of pseudo boehmite, alumina, alumina gel, sodium aluminate, aluminium phosphate, $AlCl_3$, $Al_2(SO_4)_3$, $Al(NO_3)_3$, $Al(OCH(CH_3)_2)_3$, and aluminium hydroxide. More preferably, the aluminium source includes one or more of $Al(NO_3)_3$, $Al_2(SO_4)_3$, $AlCl_3$, and $Al(OCH(CH_3)_2)_3$.

The templating agent plays an important role in the synthesis of the zeolite catalyst. In particular, the templating agent mainly has the structure-directing role in the synthesis of the zeolite catalyst. Different templating agents have a significant effect on the framework structure and properties of the zeolite catalyst according to the disclosure. The templating agent may include quaternary ammonium surfactants, which preferably include TPAOH and/or tetrapropylammonium bromide.

The solvent used herein is not particularly limited, and any suitable solvent may be used, such as, for example, a polar solvent, which may include water and alcohols. Water is preferably used as the solvent.

The zeolite precursor solution may contain $SiO_2$, the templating agent, $Al_2O_3$, and H2O at a molar ratio of 100:(30-60):(0-4):(2000-6000).

The mixing of the silicon source, the templating agent, the aluminium source, and the solvent may be carried out at room temperature for 24 to 48 hours to obtain the zeolite precursor solution.

Hydrothermal Crystallization

The zeolite precursor solution is then subjected to hydrothermal crystallization. The hydrothermal crystallization may be performed in a hydrothermal reactor, such as, for example, Teflon-lined stainless steel hydrothermal autoclave.

The hydrothermal crystallization may be carried out at a temperature of from 130 to 170° C., preferably from 140 to 160° C., for a period of time of from 2 to 15 days, preferably from 3 to 12 days.

Then, a product resulting from the hydrothermal crystallization may be subjected to steps including washing and drying. For the washing step, the product may be washed with deionized water until neutral pH. The drying step may be carried out at a temperature of from 90 to 120° C.

Calcination

The ion-exchanged zeolite with ammonium ions is subjected to calcination to obtain a precursor of the zeolite catalyst according to the present disclosure. The conditions for the calcination of the ion-exchanged zeolite are not particularly limited. For example, the calcination may be carried out at a temperature of from 300 to 650° C. for a period of time of from 4 to 12 hours.

Ion-exchange

The zeolite precursor may be ion-exchanged in an aqueous solution of $NH_4Cl$.

The conditions for the ion-exchange are not particularly limited. For example, the ion-exchange may be carried out at a temperature of from 20 to 120° C. for a period of time of from 2 to 48 hours.

A product resulting from the ion-exchange is usually subjected to steps including washing, drying, and calcination. For the washing step, the product resulting from the ion-exchange may be washed with deionized water until neutral pH. The drying step may be carried out at a temperature of from 30 to 150° C. for a period of time of from 2 to 12 hours. Then, the product may be subjected to calcination to obtain the precursor of the zeolite catalyst according to the present disclosure, which is used as a carrier in a subsequent step. The conditions for the calcination are not particularly limited. For example, the calcination may be carried out at a temperature of from 300 to 650° C. for a period of time of from 4 to 12 hours.

Impregnation

The impregnation may be carried out at a temperature of from 20 to 150° C. for a period of time of from 6 to 48 hours. In order not to affect uniform distribution of the aluminium species on the molecular sieve, the impregnation may be carried out at 20 to 40° C. for 2 to 4 hours, then at 40 to 80° C. for 2 to 4 hours, and then at 80 to 150° C. for 2 to 4 hours, for example.

Calcination

A product resulting from the impregnation is then subjected to calcination to obtain the zeolite catalyst according to the present disclosure. The conditions for the calcination are not particularly limited. For example, the calcination may be carried out at a temperature of from 300 to 650° C. for a period of time of from 4 to 12 hours.

Second Aspect

A second aspect of the present disclosure provides a zeolite catalyst prepared by the method according to the first aspect of the present disclosure. The zeolite catalyst may have an MFI structure and have an average particle size of from 200 to 500 nm, and the zeolite catalyst may have a Brønsted to Lewis acid ratio of from 0.1 to 1. The zeolite catalyst may also have a specific surface area of from 300 to 600 $m^2/g$ and a pore volume of from 0.3 to 0.7 $cm^3/g$.

Third Aspect

A third aspect of the present disclosure provides the use of the zeolite catalyst prepared by the method according to the first aspect of the present disclosure in catalytic cracking of hydrocarbons to produce propylene.

Fourth Aspect

A fourth aspect of the present disclosure provides a catalytic cracking process for producing propylene from hydrocarbons by using the zeolite catalyst prepared by the method according to the first aspect of the present disclosure as a catalyst.

EXAMPLES

The various embodiments of the present disclosure will now be described in further detail by way of the following examples, which, however, are for illustrative purposes only and should not be construed as limiting the disclosure. Conditions not indicated in the examples may be conventional or may be carried out following the manufacturer's recommendations. Reagents or instruments used in the examples without specified manufacturers can be any commercially available ones.

In the examples, TPAOH was used as the templating agent, TOES was used as the silicon source, and $Al_2(SO_4)_3 \cdot 18H_2O$ was used as the aluminium source. The water used in the examples was deionized water. All reagents were of analytical purity.

Comparative Examples 1-1 to 1-5

8.32 g of TOES, 13.0 g of TPAOH (25 aqueous solution), an amount of $Al_2(SO_4)_3 \cdot 18H_2O$ and 25.16 g of deionized water were mixed to form a mixed solution. The mixed solution was stirred at room temperature for 24 hours and was then put in an autoclave to be subjected to hydrothermal crystallization at 165° C. for 3 days. The product resulting therefrom was washed with deionized water until neutral pH, dried at 120° C., and then calcined in air atmosphere in a muffle furnace at 550° C. for 6 hours, to obtain a ZSM-5 zeolite precursor. 1 g of the ZSM-5 zeolite precursor was taken and mixed with 125 mL of a 1 mol/L solution of $NH_4Cl$. The mixture was heated in water bath to 85° C. and stirred for 3 hours. The resulting product was washed with deionized water until neutral pH, dried at 120° C. for 6 hours, and then calcined in air atmosphere in a muffle furnace at 550° C. for 6 hours, to obtain a H-type ZSM-5 zeolite catalyst.

In Comparative Example 1-1, 0.1 g of $Al_2(SO_4)_3 \cdot 18H_2O$ was used. The obtained ZSM-5 zeolite catalyst had a Si/Al ratio of 150.

In Comparative Example 1-2, 0.133 g of $Al_2(SO_4)_3 \cdot 18H_2O$ was used. The obtained ZSM-5 zeolite catalyst had a Si/Al ratio of 100.

In Comparative Example 1-3, 0.2 g of $Al_2(SO_4)_3 \cdot 18H_2O$ was used. The obtained ZSM-5 zeolite catalyst had a Si/Al ratio of 75.

In Comparative Example 1-4, 0.266 g of $Al_2(SO_4)_3 \cdot 18H_2O$ was used. The obtained ZSM-5 zeolite catalyst had a Si/Al ratio of 50.

In Comparative Example 1-5, 0.532 g of $Al_2(SO_4)_3 \cdot 18H_2O$ was used. The obtained ZSM-5 zeolite catalyst had a Si/Al ratio of 25.

The zeolite catalyst prepared in Comparative Example 1-1 was determined to have a specific surface area of 480 $m^2/g$ and a pore volume of 0.586 $cm^3/g$.

The zeolite catalyst prepared in Comparative Example 1-2 was determined to have a specific surface area of 478 $m^2/g$ and a pore volume of 0.582 $cm^3/g$.

The zeolite catalyst prepared in Comparative Example 1-3 was determined to have a specific surface area of 472 $m^2/g$ and a pore volume of 0.571 $cm^3/g$.

The zeolite catalyst prepared in Comparative Example 1-4 was determined to have a specific surface area of 467 $m^2/g$ and a pore volume of 0.563 $cm^3/g$.

The zeolite catalyst prepared in Comparative Example 1-5 was determined to have a specific surface area of 453 $m^2/g$ and a pore volume of 0.596 $cm^3/g$.

A SEM image of the zeolite catalyst prepared in Comparative Example 1-1 is shown in FIG. 1A-B. Through statistical analysis, it was found that the zeolite catalyst had a particle size within a range of from 140 to 320 nm and an average particle size of 240 nm.

Si/Al ratios of the zeolite catalysts prepared in Comparative Examples 1-1 to 1-5 were determined by ICP-AES. The results are shown in Table 1. The determined Si/Al ratios were close to their theoretical molar ratios.

Figure 4:
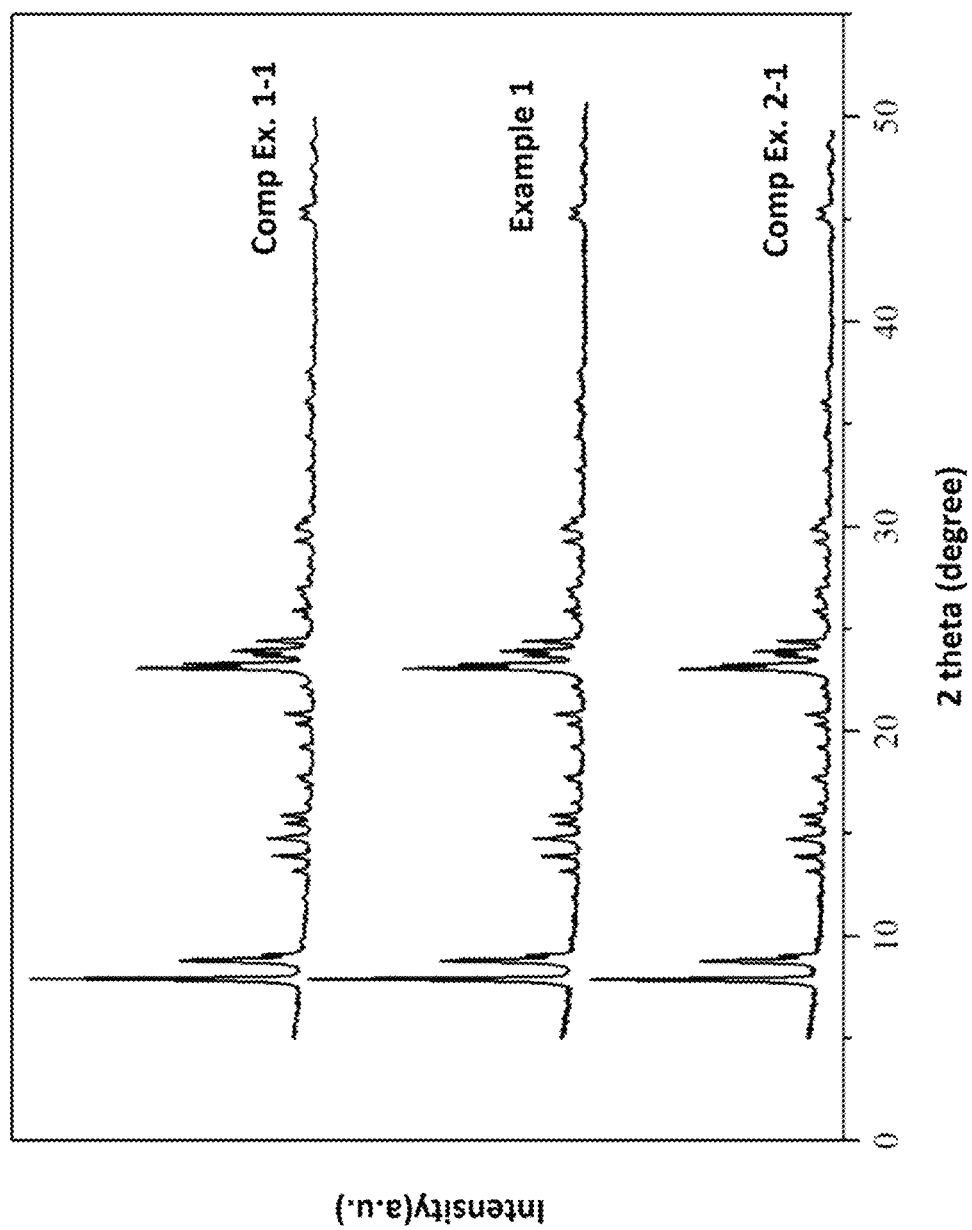
FIG. 4 shows X-ray diffraction (XRD) patterns of zeolite catalysts prepared in Comparative Example 1-1, Example 1, and Comparative Example 2-1.

An XRD pattern of the zeolite catalyst prepared in Comparative Example 1-1 is shown in FIG. 4. The XRD pattern of the zeolite catalyst was analyzed using jade software by comparison with a PDF card JCPDS-44-0003. It was found that the zeolite catalyst had an MFI structure.

Concentrations of the Brønsted and Lewis acid sites in the zeolite catalysts prepared in Comparative Examples 1-1 to 1-5, the Brønsted to Lewis acid ratio, and overall concentration of the acid sites (Brønsted and Lewis) were measured by pyridine adsorption. The results are shown in Table 2. It can be seen from the results that with the decrease in Si/Al ratio, the concentrations of the Brønsted and Lewis acid sites and the overall concentration of the acid sites each increased, and the Brønsted to Lewis acid ratios were in the range of from 0.5 to 0.57 and were thus close to each other.

Examples 1-5

8.32 g of TOES, 13.0 g of TPAOH (25% aqueous solution), 0.0665 g of $Al_2(SO_4)_3 \cdot 18H_2O$ and 25.16 g of deionized water were mixed to form a mixed solution. The mixed solution was stirred at room temperature for 24 hours and was then put in an autoclave to be subjected to hydrothermal crystallization at 165° C. for 3 days. The product resulting therefrom was washed with deionized water until neutral pH, dried at 120° C., and then calcined at 550° C. for 6 hours, to obtain a ZSM-5 zeolite precursor having a theoretical Si/Al molar ratio of 200. 1 g of the ZSM-5 zeolite precursor was taken and mixed with 125 mL of a 1 mol/L solution of $NH_4Cl$. The mixture was heated in water bath to 85° C. and stirred for 3 hours. The resulting product was washed with deionized water until neutral pH, dried at 120° C. for 6 hours, and then calcined in air atmosphere in a muffle furnace at 550° C. for 6 hours, to obtain a H-type ZSM-5 zeolite catalyst carrier.

An amount of $Al_2(SO_4)_3 \cdot 18H_2O$ was dissolved in deionized water to prepare an Al-containing solution (i.e., $Al_2(SO_4)_3$ solution) having a concentration of from 0.5 to 10.5% by weight. 1.8 g of the Al-containing solution was added dropwise to 1 g of the catalyst carrier obtained above and continuously stirred until well mixed. The mixture was dried at 30° C. for 12 hours, then at 60° C. for another 12 hours, and then at 120° C. for a further 12 hours. After completion of the drying, the mixture was calcined in air atmosphere in a muffle furnace at 550° C. for 6 hours to obtain a Al-modified ZSM-5 zeolite catalyst according to the present disclosure.

In Example 1, the $Al_2(SO_4)_3$ solution used had a concentration of 0.5% by weight. The zeolite catalyst had a theoretical Si/Al (framework Al and EFAL species) ratio of 150. The zeolite catalyst prepared in Comparative Example 1-1 had the same theoretical Si/Al ratio as the zeolite catalyst prepared in Example 1, and was used for comparison with the latter.

In Example 2, the $Al_2(SO_4)_3$ solution used had a concentration of 1.53%. The zeolite catalyst had a theoretical Si/Al ratio of 100. The zeolite catalyst prepared in Comparative Example 1-2 had the same theoretical Si/Al ratio as the zeolite catalyst prepared in Example 2, and was used for comparison with the latter.

In Example 3, the $Al_2(SO_4)_3$ solution used had a concentration of 2.55%. The zeolite catalyst had a theoretical Si/Al ratio of 75. The zeolite catalyst prepared in Comparative Example 1-3 had the same theoretical Si/Al ratio as the zeolite catalyst prepared in Example 3, and was used for comparison with the latter.

In Example 4, the $Al_2(SO_4)_3$ solution used had a concentration of 4.5%. The zeolite catalyst had a theoretical Si/Al ratio of 50. The zeolite catalyst prepared in Comparative Example 1-4 had the same theoretical Si/Al ratio as the zeolite catalyst prepared in Example 4, and was used for comparison with the latter.

In Example 5, the $Al_2(SO_4)_3$ solution used had a concentration of 10.5%. The zeolite catalyst had a theoretical Si/Al ratio of 25. The zeolite catalyst prepared in Comparative Example 1-5 had the same theoretical Si/Al ratio as the zeolite catalyst prepared in Example 5, and was used for comparison with the latter.

The zeolite catalyst prepared in Example 1 was determined to have a specific surface area of 458 $m^2/g$ and a pore volume of 0.471 $cm^3/g$.

The zeolite catalyst prepared in Example 2 was determined to have a specific surface area of 456 $m^2/g$ and a pore volume of 0.469 $cm^3/g$.

The zeolite catalyst prepared in Example 3 was determined to have a specific surface area of 461 $m^2/g$ and a pore volume of 0.493 $cm^3/g$.

The zeolite catalyst prepared in Example 4 was determined to have a specific surface area of 462 $m^2/g$ and a pore volume of 0.468 $cm^3/g$.

The zeolite catalyst prepared in Example 5 was determined to have a specific surface area of 453 $m^2/g$ and a pore volume of 0.482 $cm^3/g$.

Si/Al ratios of the zeolite catalysts prepared in Examples 1-5 were determined by ICP-AES. The results are shown in Table 1. The determined Si/Al ratios were close to their theoretical molar ratios.

Figure 2B:
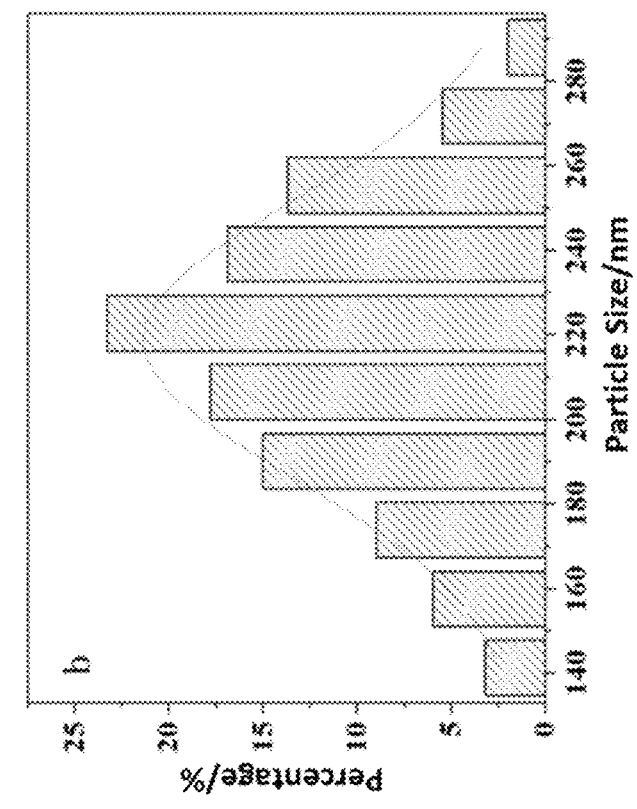
FIG. 2A-B shows (a) a SEM image, and (b) particle size distribution, of a zeolite catalyst prepared in Example 1.
Figure 2A:
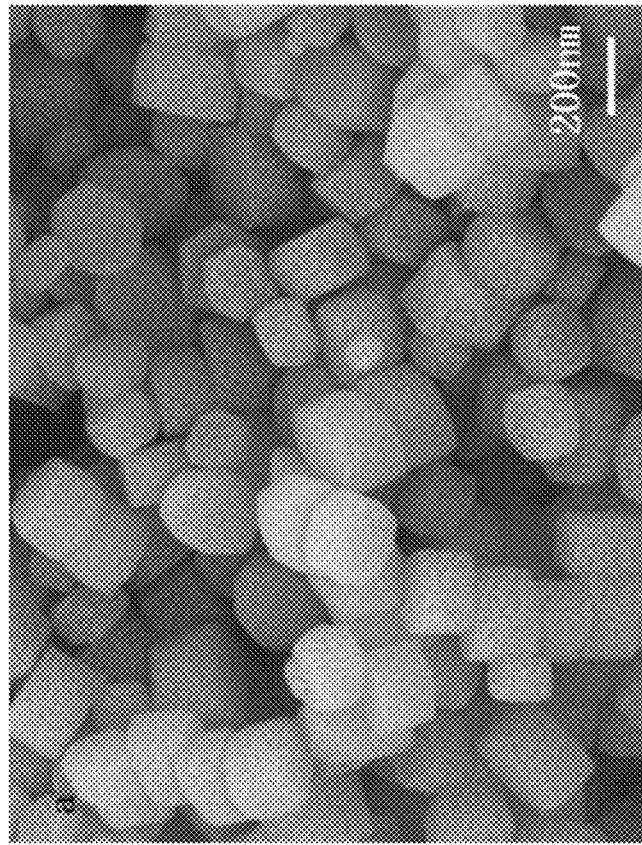

A SEM image of the zeolite catalyst prepared in Example 1 is shown in FIG. 2. Through statistical analysis, it was found that the zeolite catalyst had a particle size within a range of from 150 to 350 nm and an average particle size of 240 nm.

An XRD pattern of the zeolite catalyst prepared in Example 1 is shown in FIG. 4. The XRD pattern of the zeolite catalyst was analyzed using jade software by comparison with a PDF card JCPDS-44-0003. It was found that the zeolite catalyst had an MFI structure. This indicates that the type of the zeolite catalyst was not changed by the modification thereof with Al species.

Concentrations of the Brønsted and Lewis acid sites in the zeolite catalysts prepared in Examples 1-5, the Brønsted to Lewis acid ratio, and overall concentration of the acid sites (Brønsted and Lewis) were measured by pyridine adsorption. The results are shown in Table 2.

By comparing the results for the zeolite catalysts prepared in Comparative Example 1-1 and in Example 1 which had similar Si/Al ratios, it was found that their overall concentrations of the acid sites were close to each other, but the Brønsted to Lewis acid ratio of the zeolite catalyst prepared in Example 1 was lower than that of the zeolite catalyst prepared in Comparative Example 1-1. The same conclusion was also obtained between Example 2 and Comparative Example 1-2, between Example 3 and Comparative Example 1-3, between Example 4 and Comparative Example 1-4, and between Example 5 and Comparative Example 1-5.

As described above, the concentrations of the Brønsted and Lewis acid sites in the zeolite catalysts prepared in Comparative Examples 1-1 to 1-5 and the overall concentration of the acid sites each increased with the decrease in Si/Al ratio, and the Brønsted to Lewis acid ratios of these zeolite catalysts were in the range of from 0.5 to 0.57. In contrast, the Brønsted to Lewis acid ratios of the zeolite catalysts prepared in Examples 1-5 decreased as the Al content in the $Al_2(SO_4)_3$ solution increased. Specifically, the Brønsted to Lewis acid ratios of the zeolite catalysts prepared in Examples 1-5 varied in the range of from 0.1 to 1, indicating that the Brønsted to Lewis acid ratios varied in a wide range. The Brønsted to Lewis acid ratios in the decreasing order is Example 1>Example 2>Example 3>Example 4>Example 5. So, the Brønsted to Lewis acid ratio was negatively correlated with the loading amount of the EFAL species.

Comparative Examples 2-1 to 2-5

A series of Fe-modified ZSM-5 zeolites which have been widely reported were prepared for comparison with the zeolite catalysts according to the present disclosure. Distributions of the acid sites in the Fe-modified ZSM-5 zeolites were analyzed.

8.32 g of TOES, 13.0 g of TPAOH (25% aqueous solution), 0.0665 g of $Al_2(SO_4)_3 \cdot 18H_2O$ and 25.16 g of deionized water were mixed to form a mixed solution. The mixed solution was stirred at room temperature for 24 hours and was then put in an autoclave to be subjected to hydrothermal crystallization at 165° C. for 3 days. The product resulting therefrom was washed with deionized water until neutral pH, dried at 120° C., and then calcined at 550° C. for 6 hours, to obtain a ZSM-5 zeolite precursor. 1 g of the ZSM-5 zeolite precursor was taken and mixed with 125 mL of a 1 mol/L solution of $NH_4Cl$. The mixture was heated in water bath to 85° C. and stirred for 3 hours. The resulting product was washed with deionized water until neutral pH, dried at 120° C. for 6 hours, and then calcined in air atmosphere in a muffle furnace at 550° C. for 6 hours, to obtain a H-type ZSM-5 zeolite catalyst carrier.

An amount of ferric sulfate ($Fe_2(SO_4)_3$) was dissolved in deionized water to prepare a series of Fe-containing solutions (i.e., $Fe_2(SO_4)_3$ solutions having a concentration of from 0.3 to 6.3% by weight. 1.8 g of the Fe-containing solution was added dropwise to 1 g of the catalyst carrier obtained above and continuously stirred until well mixed. The mixture was dried at 30° C. for 12 hours, then at 60° C. for another 12 hours, and then at 120° C. for a further 12 hours. After completion of the drying, the mixture was calcined in air atmosphere at 550° C. for 6 hours to obtain a Fe-modified ZSM-5 zeolite catalyst.

In Comparative Example 2-1, the $Fe_2(SO_4)_3$ solution had a concentration of 0.3% by weight. The zeolite catalyst had a theoretical Si/(Al+Fe) ratio of 150. The zeolite catalyst prepared in Comparative Example 2-1 was used for comparison with the catalyst prepared in Example 1.

In Comparative Example 2-2, the $Fe_2(SO_4)_3$ solution had a concentration of 0.918% by weight. The zeolite catalyst had a theoretical Si/(Al+Fe) ratio of 100. The zeolite catalyst prepared in Comparative Example 2-2 was used for comparison with the catalyst prepared in Example 2

In Comparative Example 2-3, the $Fe_2(SO_4)_3$ solution had a concentration of 1.53% by weight. The zeolite catalyst had a theoretical Si/(Al+Fe) ratio of 75. The zeolite catalyst prepared in Comparative Example 2-3 was used for comparison with the catalyst prepared in Example 3.

In Comparative Example 2-4, the $Fe_2(SO_4)_3$ solution had a concentration of 2.7% by weight. The zeolite catalyst had a theoretical Si/(Al+Fe) ratio of 50. The zeolite catalyst prepared in Comparative Example 2-4 was used for comparison with the catalyst prepared in Example 4.

In Comparative Example 2-5, the $Fe_2(SO_4)_3$ solution had a concentration of 6.3% by weight. The zeolite catalyst had a theoretical Si/(Al+Fe) ratio of 25. The zeolite catalyst prepared in Comparative Example 2-5 was used for comparison with the catalyst prepared in Example 5.

The zeolite catalyst prepared in Comparative Example 2-1 was determined to have a specific surface area of 432 $m^2/g$ and a pore volume of 0.536 $cm^3/g$.

The zeolite catalyst prepared in Comparative Example 2-2 was determined to have a specific surface area of 430 $m^2/g$ and a pore volume of 0.543 $cm^3/g$.

The zeolite catalyst prepared in Comparative Example 2-3 was determined to have a specific surface area of 428 $m^2/g$ and a pore volume of 0.554 $cm^3/g$.

The zeolite catalyst prepared in Comparative Example 2-4 was determined to have a specific surface area of 425 $m^2/g$ and a pore volume of 0.561 $cm^3/g$.

The zeolite catalyst prepared in Comparative Example 2-5 was determined to have a specific surface area of 421 $m^2/g$ and a pore volume of 0.539 $cm^3/g$.

Figures 3A, 3B:
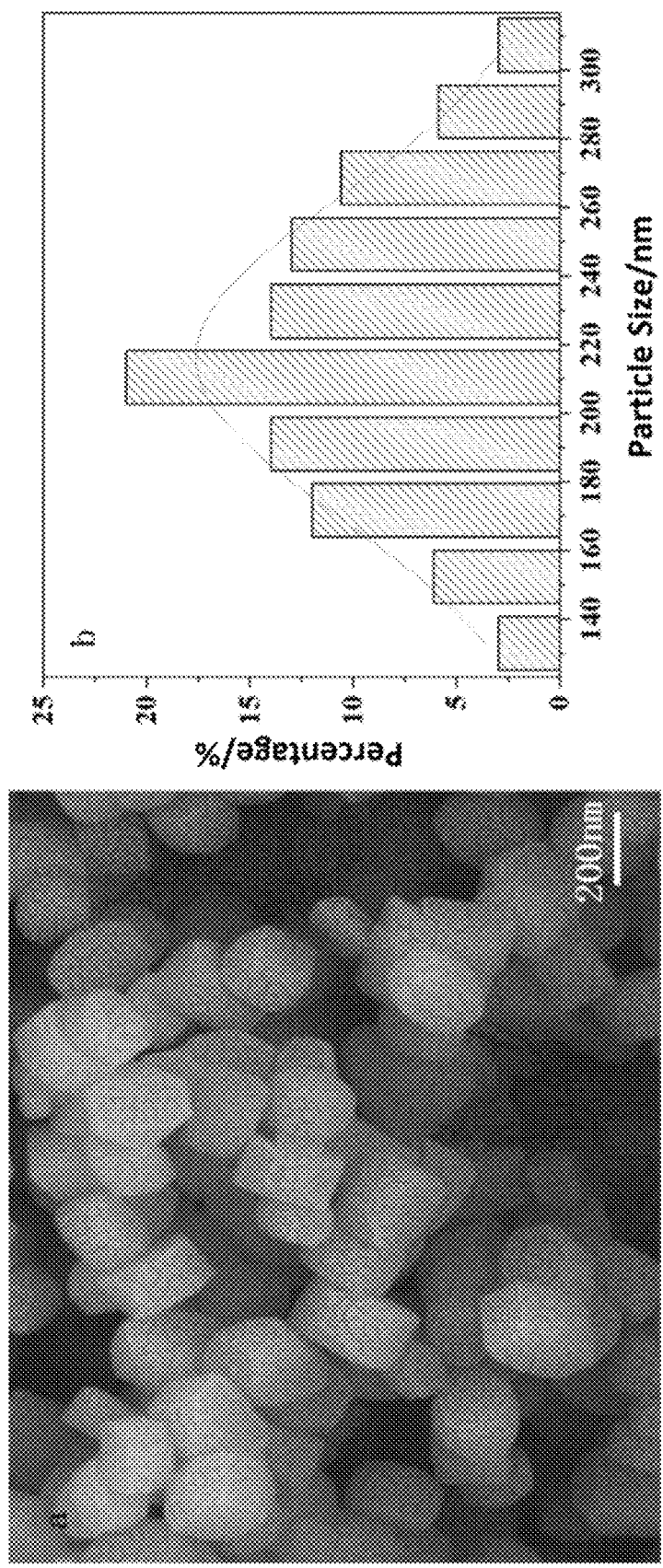
FIG. 3A-B shows (a) a SEM image, and (b) particle size distribution, of a zeolite catalyst prepared in Comparative Example 2-1.

A SEM image of the zeolite catalyst prepared in Comparative Example 2-1 is shown in FIG. 3. Through statistical analysis, it was found that the zeolite catalyst had a particle size within the range of from 120 to 320 nm and an average particle size of 210 nm.

An XRD pattern of the zeolite catalyst prepared in Comparative Example 2-1 is shown in FIG. 4. The XRD pattern of the zeolite catalyst was analyzed using jade software by comparison with a PDF card JCPDS-44-0003. It was found that the zeolite catalyst had an MFI structure. This indicates that the type of the zeolite catalyst was not changed by the modification thereof with Fe species.

TABLE 1

|  | Si/Al ratio |
|---|---|
| Comp Ex. 1-1 | 145 |
| Comp Ex. 1-2 | 97 |
| Comp Ex. 1-3 | 73 |
| Comp Ex. 1-4 | 45 |
| Comp Ex. 1-5 | 22 |
| Ex. 1 | 143 |
| Ex. 2 | 95 |
| Ex. 3 | 70 |
| Ex. 4 | 47 |
| Ex. 5 | 23 |
| Comp Ex. 2-2 | 96 |
| Comp Ex. 2-3 | 73 |

TABLE 2

| Comparative Examples 3-1 and 3-2 | | | | |
|---|---|---|---|---|
|  | Bronsted acid ($\mu mol \cdot g^{-1} NH_3$) | Lewis acid ($\mu mol \cdot g^{-1} NH_3$) | Bronsted to Lewis acid molar ratio | Overall Concentration of acid sites ($\mu mol \cdot g^{-1} NH_3$) |
| Comp Ex. 1-1 | 81 | 142 | 0.57 | 223 |
| Comp Ex. 1-2 | 126 | 230 | 0.55 | 356 |
| Comp Ex. 1-3 | 161 | 304 | 0.53 | 465 |
| Comp Ex. 1-4 | 203 | 398 | 0.51 | 601 |
| Comp Ex. 1-5 | 341 | 682 | 0.50 | 1023 |
| Ex. 1 | 74 | 160 | 0.46 | 234 |
| Ex. 2 | 112 | 266 | 0.42 | 378 |
| Ex. 3 | 139 | 353 | 0.39 | 492 |
| Ex. 4 | 163 | 462 | 0.35 | 625 |
| Ex. 5 | 181 | 857 | 0.21 | 1038 |

TABLE 2-continued

Comparative Examples 3-1 and 3-2

| | Bronsted acid (μmol · g$^{-1}$ NH$_3$) | Lewis acid (μmol · g$^{-1}$ NH$_3$) | Bronsted to Lewis acid molar ratio | Overall Concentration of acid sites (μmol · g$^{-1}$ NH$_3$) |
|---|---|---|---|---|
| Comp Ex. 2-2 | 115 | 250 | 0.46 | 365 |
| Comp Ex. 2-3 | 156 | 317 | 0.49 | 473 |

Al-modified ZSM-5 zeolites which have been reported were prepared without calcination for comparison with the zeolites catalysts according to the present disclosure.

8.32 g of TOES, 13.0 g of TPAOH (25% aqueous solution), 0.0665 g of Al$_2$(SO$_4$)$_3$·18H$_2$O and 25.16 g of deionized water were mixed to form a mixed solution. The mixed solution was stirred at room temperature for 24 hours and was then put in an autoclave to be subjected to hydrothermal crystallization at 165° C. for 3 days. The product (powder form) resulting therefrom was washed with deionized water until neutral pH, dried at 120° C., and then calcined at 550° C. for 6 hours, to obtain a ZSM-5 zeolite precursor having a theoretical Si/Al molar ratio of 200. 1 g of the ZSM-5 zeolite precursor was taken and mixed with 125 mL of a 1 mol/L solution of NH$_4$Cl. The mixture was heated in water bath to 85° C. and stirred for 3 hours. The resulting product was washed with deionized water until neutral pH, dried at 120° C. for 6 hours, and then calcined in air atmosphere in a muffle furnace at 550° C. for 6 hours, to obtain a H-type ZSM-5 zeolite catalyst carrier.

An amount of Al$_2$(SO$_4$)$_3$·18H$_2$O was dissolved in deionized water to prepare Al-containing solutions (i.e., Al$_2$(SO$_4$)$_3$ solution) having a concentration of 0.5% and 10.5% by weight, respectively. 1.8 g of the Al-containing solution was added dropwise to 1 g of the catalyst carrier obtained above and continuously stirred until well mixed. The mixture was dried at 30° C. for 12 hours, then at 60° C. for another 12 hours, and then at 120° C. for a further 12 hours to obtain an Al-modified ZSM-5 zeolite catalyst without calcination.

In Comparative Example 3-1, the Al$_2$(SO$_4$)$_3$ solution had a concentration of 0.5% by weight. The zeolite catalyst had a theoretical Si/Al ratio of 150. The zeolite catalyst prepared in Comparative Example 3-1 was used for comparison with the catalyst prepared in Example 1.

In Comparative Example 3-2, the Al$_2$(SO$_4$)$_3$ solution had a concentration of 10.5% by weight. The zeolite catalyst had a theoretical SiAl ratio of 25. The zeolite catalyst prepared in Comparative Example 3-2 was used for comparison with the catalyst prepared in Example 5.

Reaction Example 1

The zeolite catalysts prepared in Comparative Example 1-1, Example 1, and Comparative Example 2-1, having a theoretical Si/Al ratio of 150, were each used in catalytic cracking of n-heptane. 0.2 g of the zeolite catalyst was mixed with 2 g of SiC filllter and then charged into a fixed bed reactor tube. The mixture was heated to 550° C. at a heating rate of 5° C/min. n-heptane was pumped into the reactor tube at a rate of 0.05 mL/h. Nitrogen gas was introduced there into at a rate of 15 mL/min. The preheating temperature was controlled at 300° C. and the reaction was controlled at 550° C. The products were analyzed by gas chromatography (GC).

FIG. 5A-D shows comparisons of (a) conversion rates of n-heptane, (b) yields of propylene, (c) selectivities of ethylene and propylene, and (d) propylene to ethylene molar ratios ($n_{propylene}/n_{ethylene}$), achieved by the zeolite catalysts prepared in Comparative Example 1-1, Example 1, and Comparative Example 2-1.

Figure 5A:
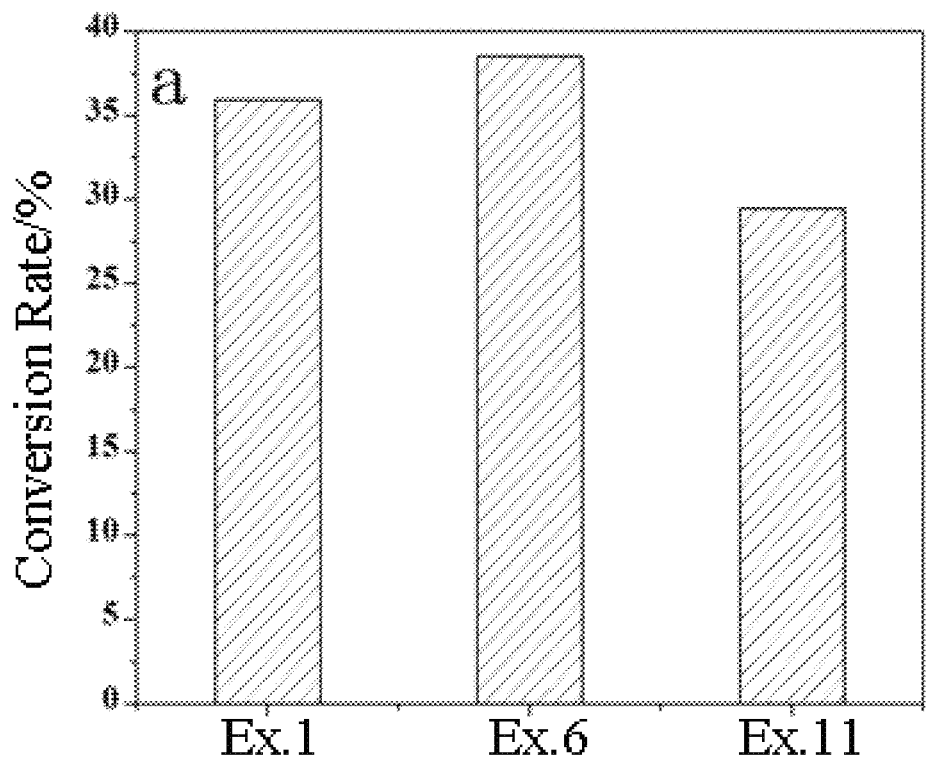
FIG. 5A-D shows comparisons of (a) conversion rates of n-heptane, (b) yields of propylene, (c) selectivities of ethylene and propylene, and (d) propylene to ethylene molar ratios ($n_{propylene}/n_{ethylene}$), achieved by zeolite catalysts prepared in Comparative Example 1-1, Example 1, and Comparative Example 2-1 when the catalytic cracking of n-heptane was carried out at 550° C.
Figure 5B:
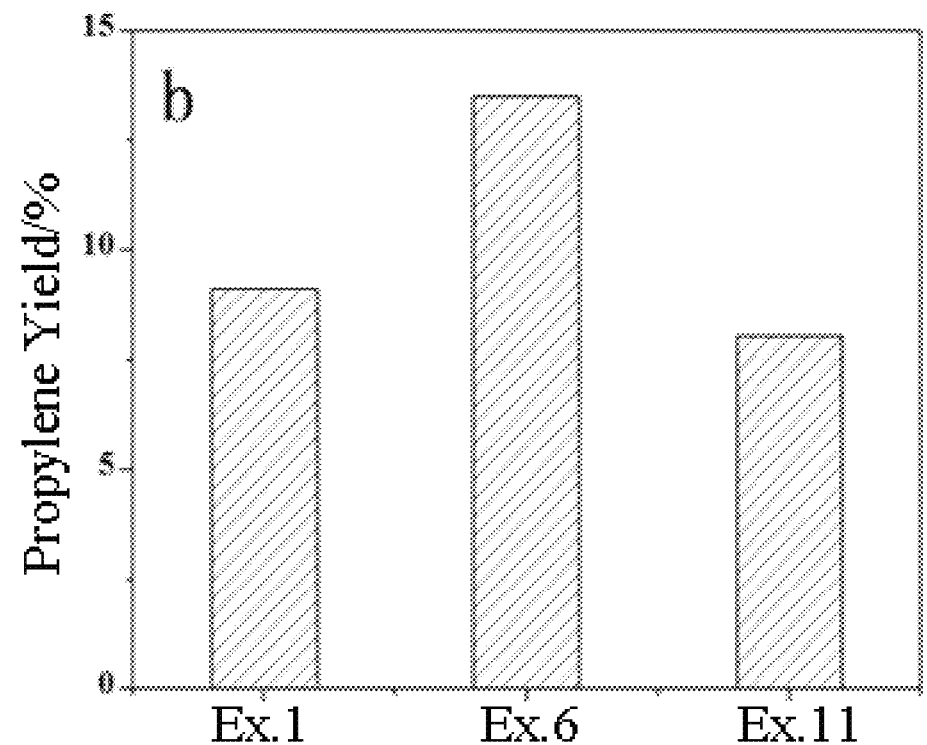
Figure 5C:
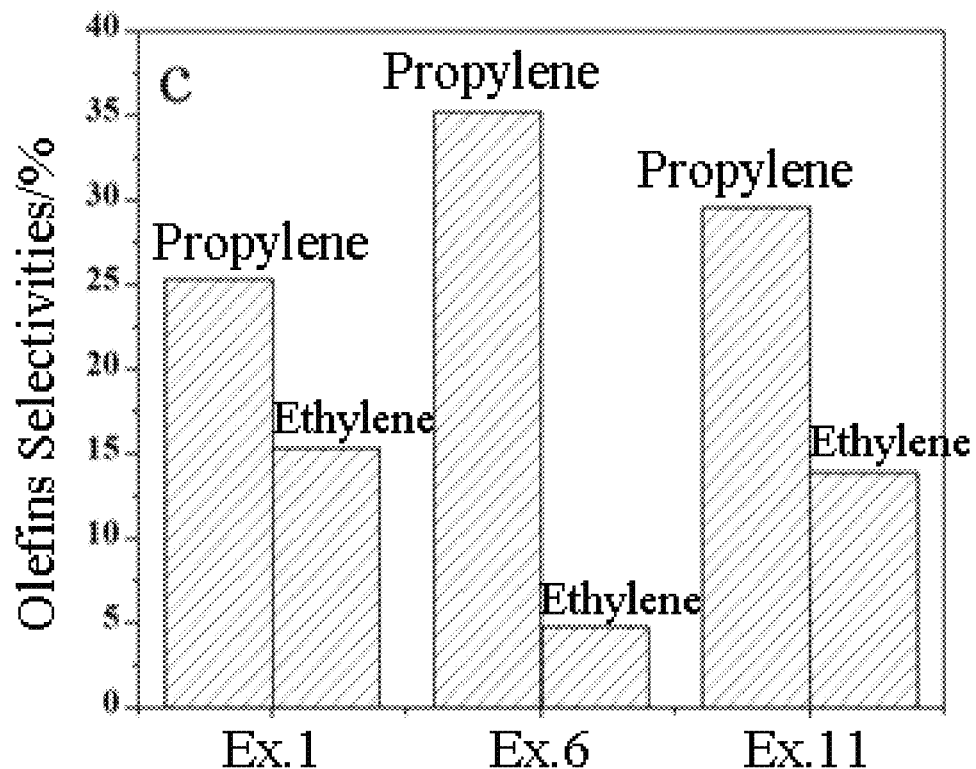
Figure 5D:
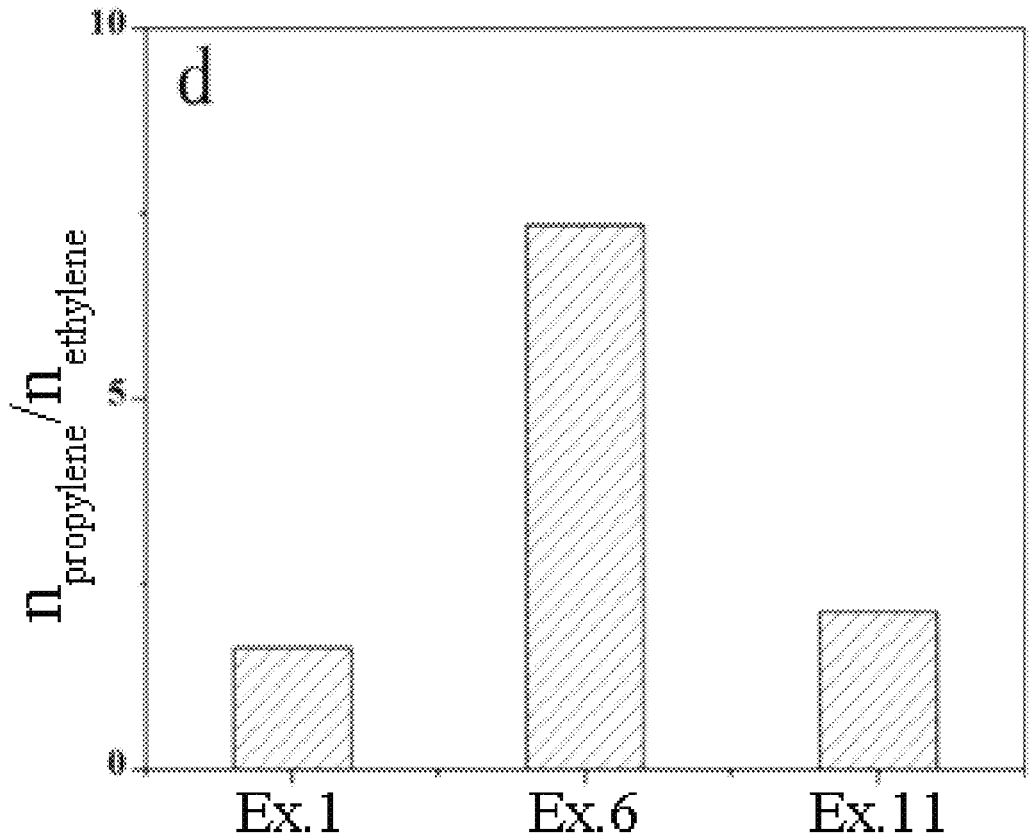
Figure 6A:
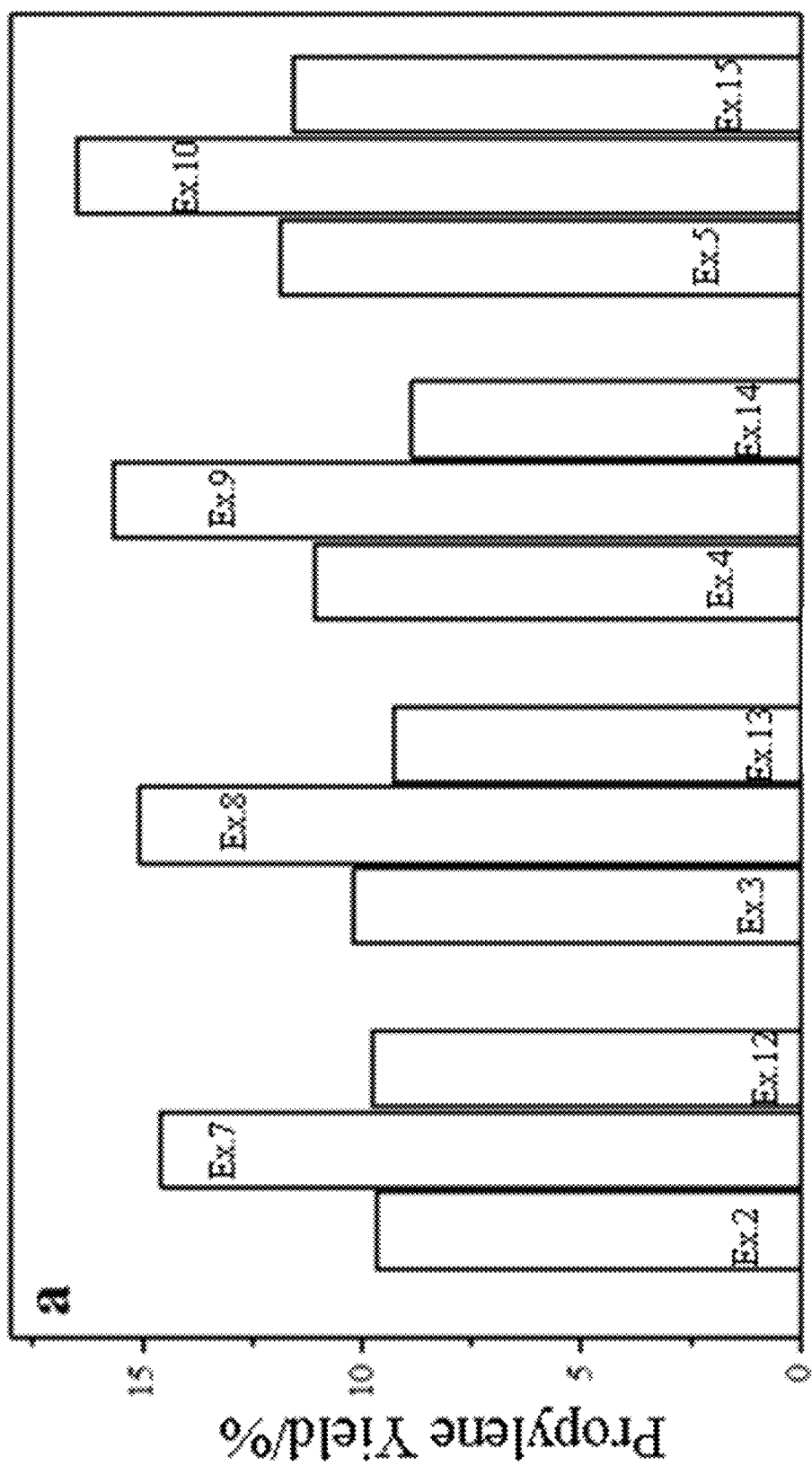
FIG. 6A-B shows comparisons of (a) yields of propylene, and (b) $n_{propylene}/n_{ethylene}$ ratios, achieved by zeolite catalysts prepared in Comparative Examples 1-2 to 1-5, Examples 2-5, and Comparative Examples 2-2 to 2-5 when the catalytic cracking of n-heptane was carried out at 550° C.
Figure 6B:
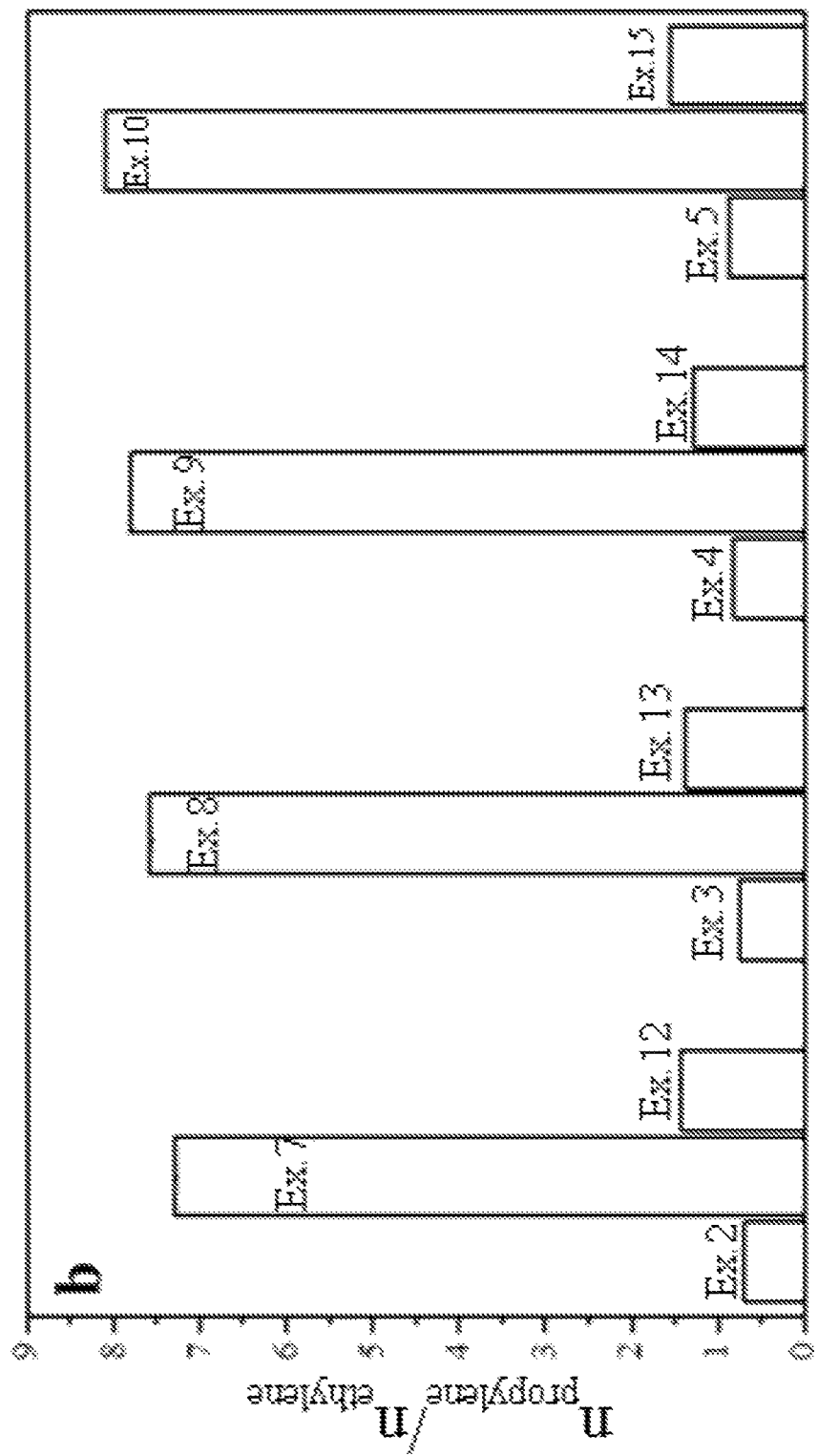

As shown in FIG. 5A-D, the zeolite catalyst prepared in Comparative Example 1-1 exhibited n-heptane conversion ratio of 35.9% (FIG. 5A), propylene yield of 9.12% (FIG. 5B), propylene selectivity of 25.3% (FIG. 5C), and propylene to ethylene molar ratio of 1.65 (FIG. 5D).

The zeolite catalyst prepared in Example 1 exhibited n-heptane conversion ratio of 33.6% (FIG. 5A), propylene yield of 11.81% (FIG. 5B), propylene selectivity of 35.1% (FIG. 5C), and propylene to ethylene molar ratio of 7.35 (FIG. 5D).

The zeolite catalyst prepared in Comparative Example 2-1 exhibited n-heptane conversion ratio of 29.47% (FIG. 5A), propylene yield of 8.06% (FIG. 5B), propylene selectivity of 29.5% (FIG. 5D), and propylene to ethylene molar ratio of 2.13 (FIG. 5D).

Apparently, the propylene yield achieved by the zeolite catalyst prepared in Example 1 was substantially higher than those achieved by the unmodified and Fe-modified zeolite catalysts prepared in Comparative Examples 1-1 and 2-1, respectively, under the same reaction conditions. By combining these results and the Brønsted to Lewis acid ratios determined by Py-IR characterization, it was found that the modification of the zeolite catalyst with Al species can lead to a lower Brønsted to Lewis acid ratio, which can facilitate the formation of propylene FIG. 6A-D shows comparisons of (a) yields of propylene, and (b) $n_{propylene}/n_{ethylene}$ ratios, achieved by the zeolite catalysts prepared in Comparative Examples 1-2 to 1-5, Examples 2 to 5, and Comparative Examples 2-2 to 2-5 when the catalytic cracking of n-heptane was carried out at 550° C. It can be seen from this figure that the Al-modified zeolite catalysts exhibited higher propylene yields and propylene to ethylene molar ratios than the unmodified and Fe-modified zeolite catalysts.

Reaction Example 2

This Example was provided to investigate the n-heptane conversion activities over different zeolite catalysts prepared above under a higher temperature and the selectivities of the cracking products. The zeolite catalysts prepared in Comparative Example 1-1, Example 1, and Comparative Example 2-1, having a theoretical Si/Al ratio of 150, were each used in catalytic cracking of n-heptane. 0.2 g of the zeolite catalyst was mixed with 2 g of SiC filter and then charged into a fixed bed reactor tube. The mixture was heated to 650° C. at a heating rate of 5° C/min. n-heptane was pumped into the reactor tube at a rate of 0.05 mL/h. Nitrogen gas was introduced thereinto at a rate of 15 mL/min. The preheating temperature was controlled at 300° C. and the reaction reaction was controlled at 650° C. The products were analyzed on-line by GC.

FIG. 7A-D shows comparisons of (a) conversion rates of n-heptane, (b) yields of propylene, (c) selectivities of ethylene and propylene, and (d) $n_{propylene}/n_{ethylene}$ ratios, achieved by these zeolite catalysts.

Figure 7A:
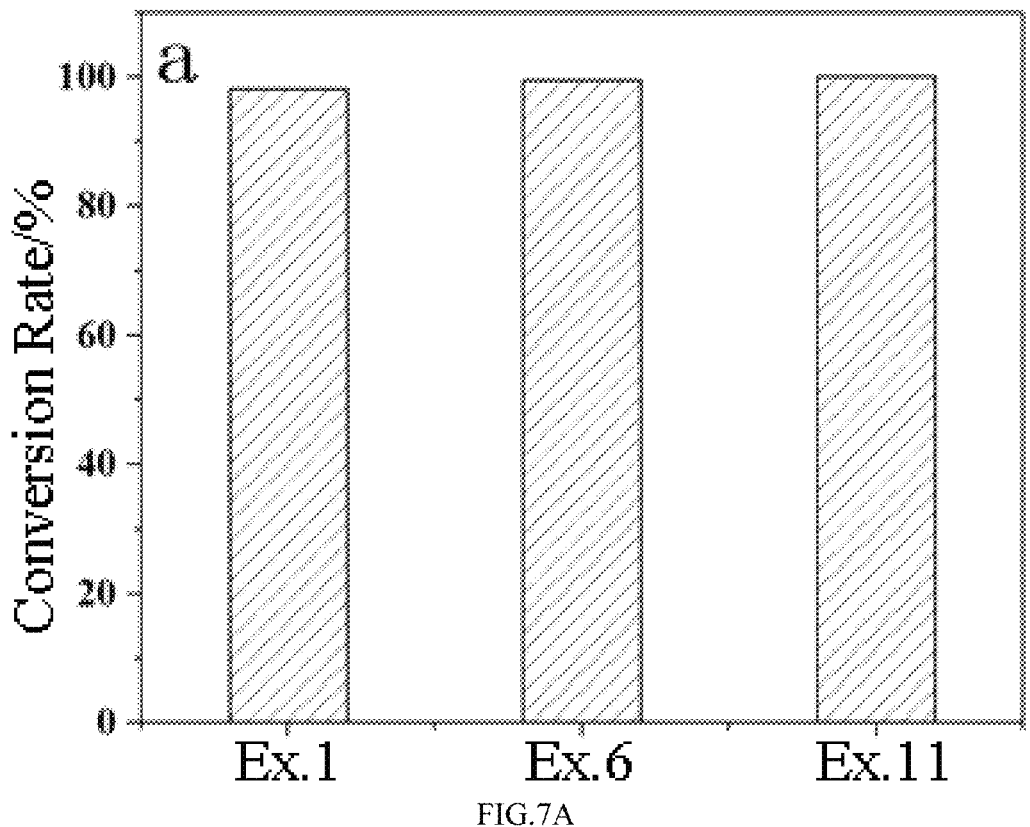
FIG. 7A-D shows comparisons of (a) conversion rates of n-heptane, (b) yields of propylene, (c) selectivities of ethylene and propylene, and (d) $n_{propylene}/n_{ethylene}$ ratios, achieved by zeolite catalysts prepared in Comparative Example 1-1, Example 1, and Comparative Example 2-1 when the catalytic cracking of n-heptane was carried out at 650° C.
Figure 7B:
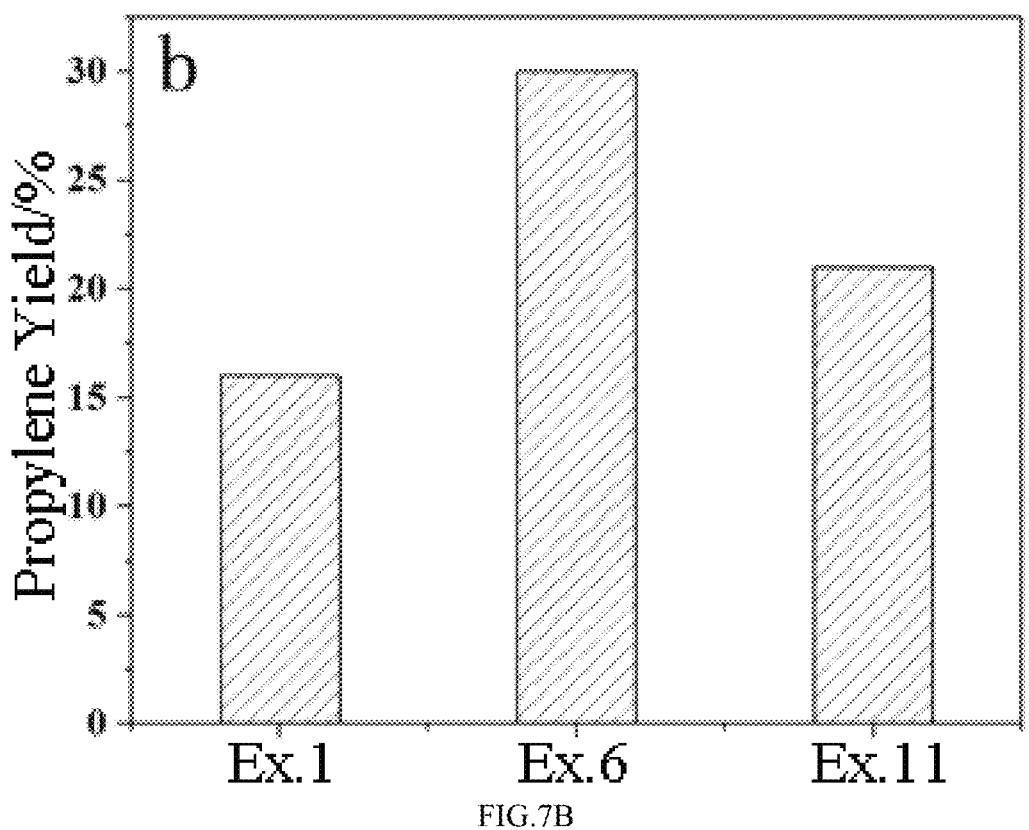
Figure 7C:
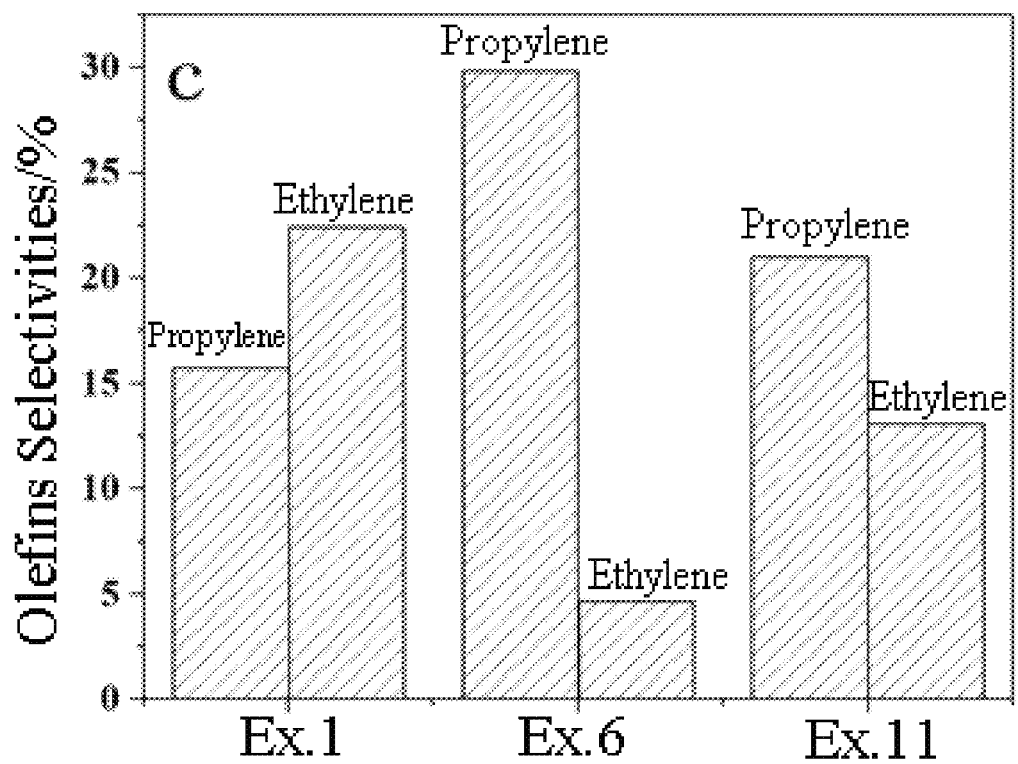
Figure 7D:
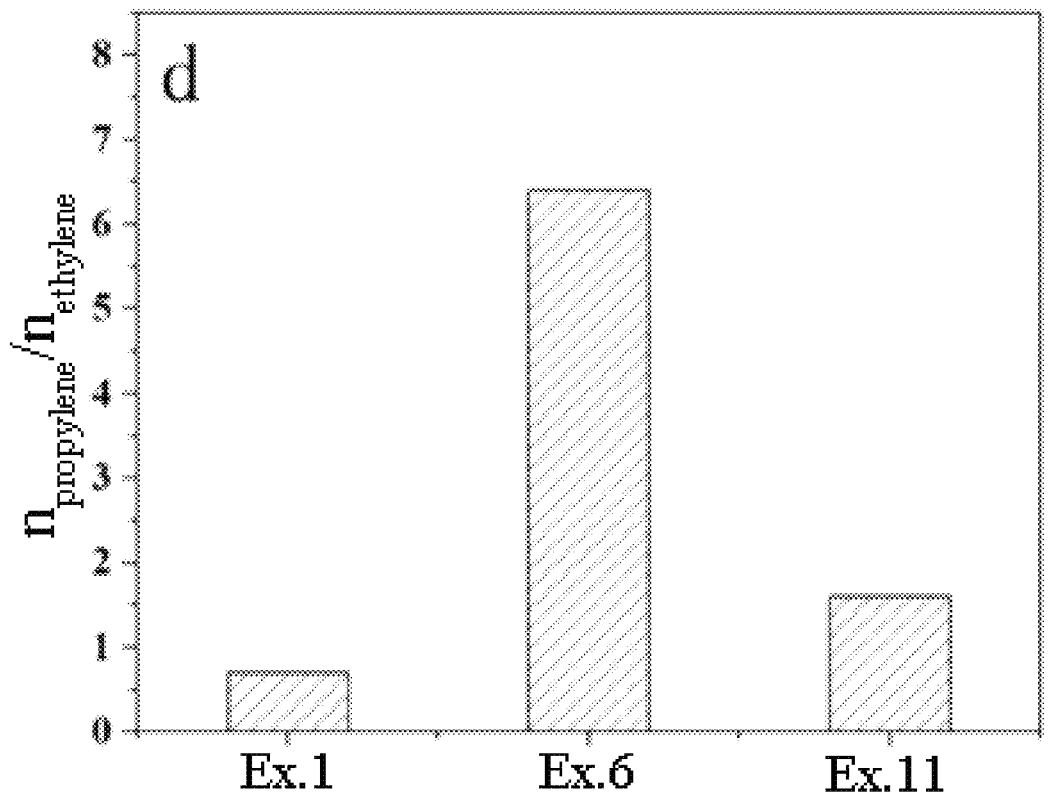
Figure 8A:
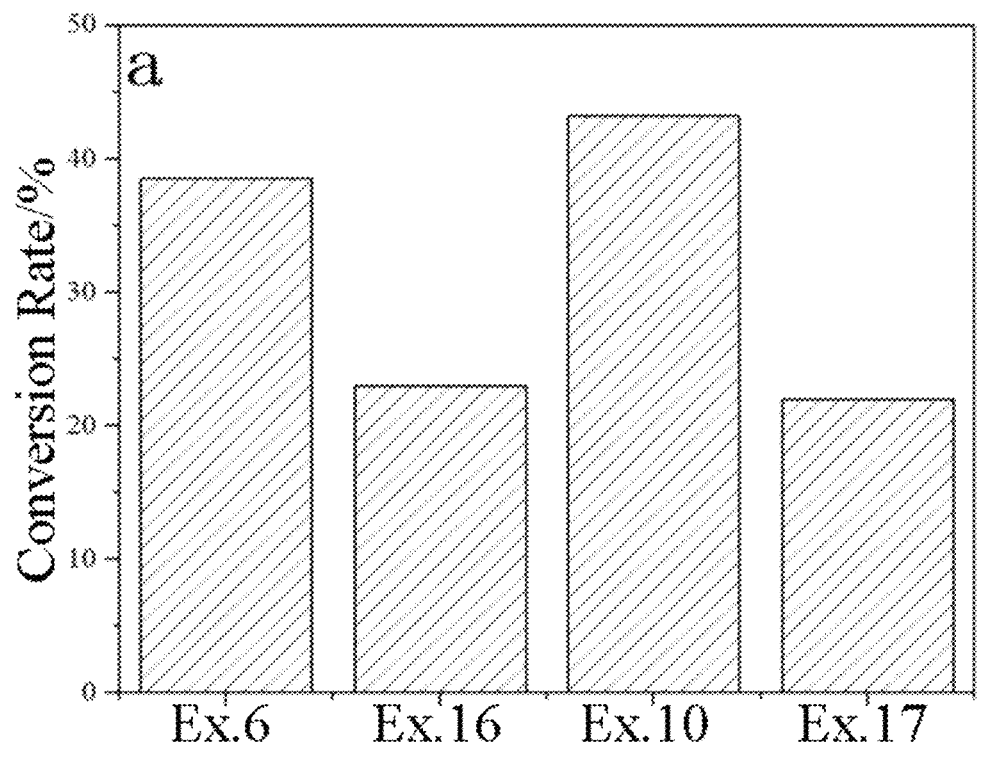
FIG. 8A-D shows comparisons of (a) conversion rates of n-heptane, (b) yields of propylene, (c) selectivities of ethylene and propylene, and (d) $n_{propylene}/n_{ethylene}$ ratios, achieved by zeolite catalysts prepared in Examples 1 and 5 and Comparative Examples 3-1 and 3-2 when the catalytic cracking of n-heptane was carried out at 550° C.
Figure 8B:
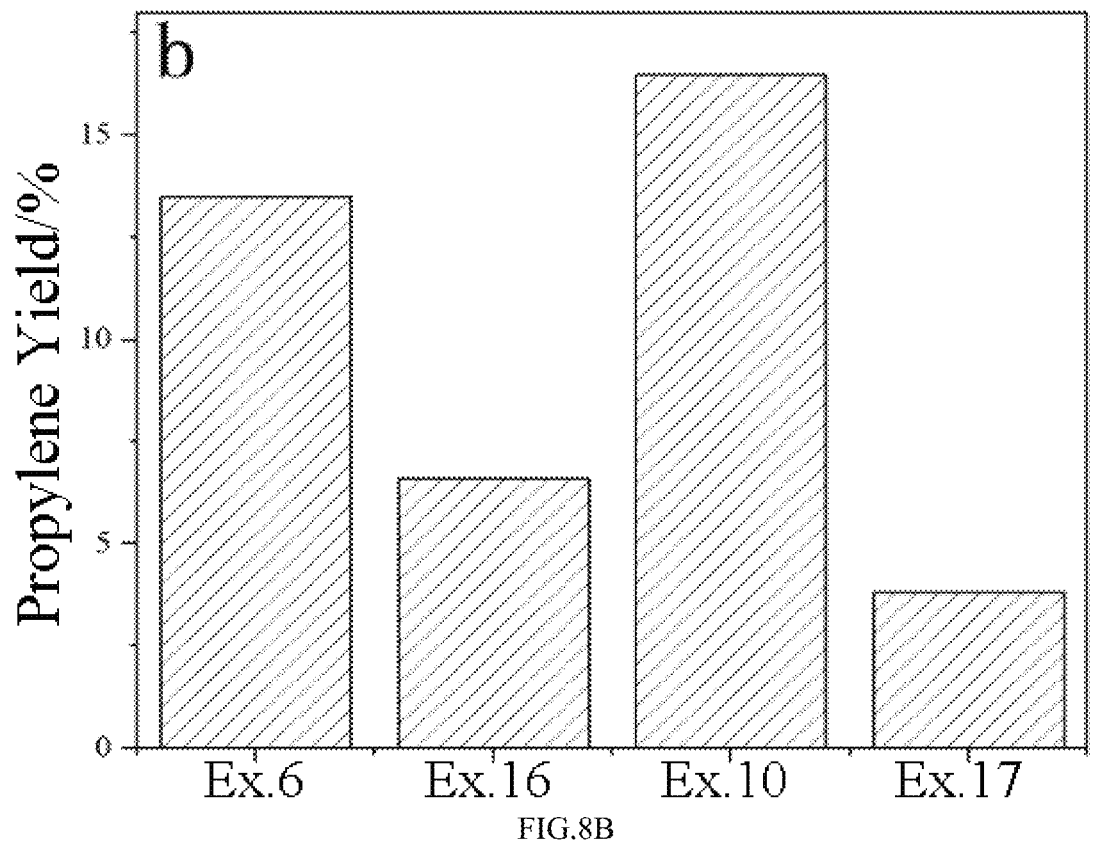
Figure 8C:
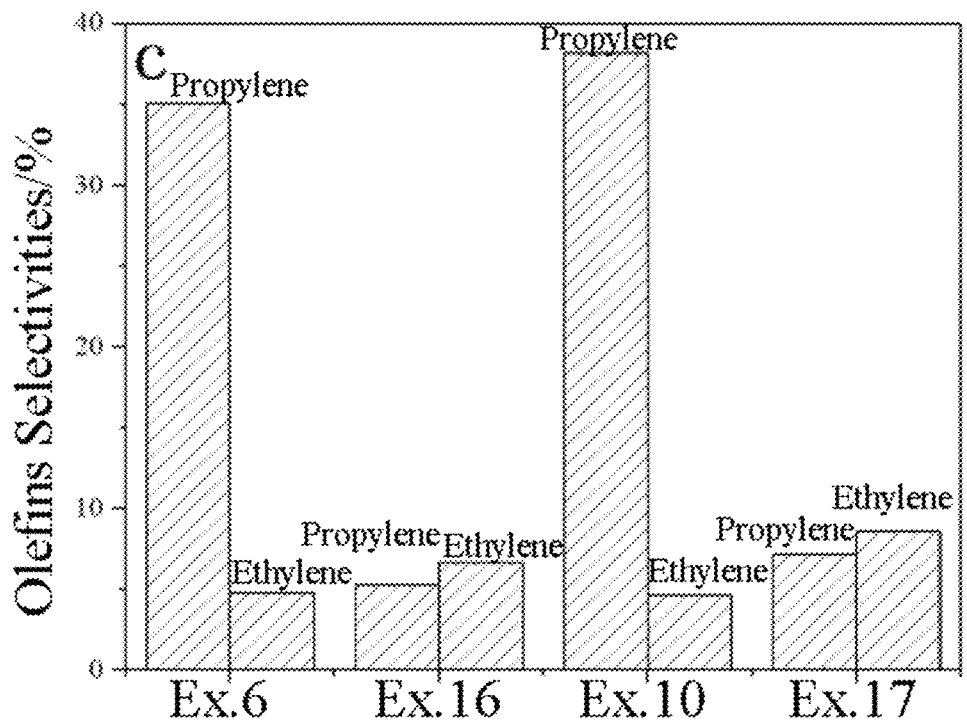
Figure 8D:
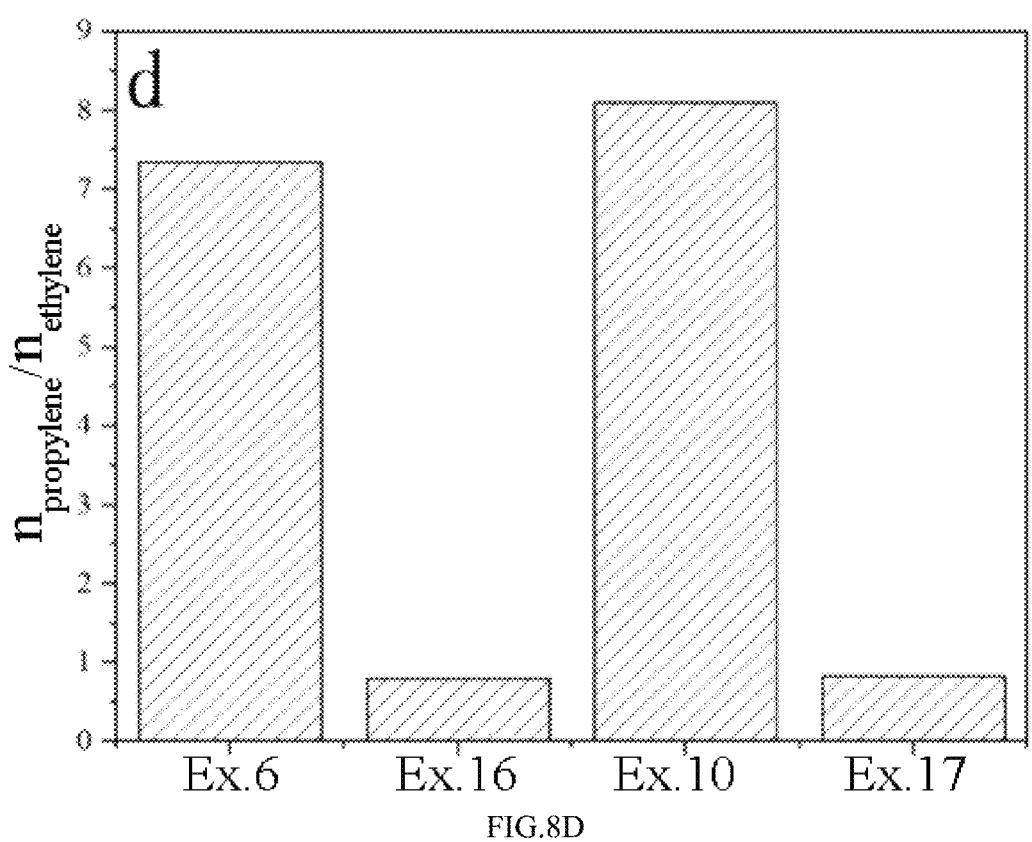

As shown in FIG. 7A-D, the zeolite catalyst prepared in Comparative Example 1-1 exhibited n-heptane conversion ratio of 98.2% (FIG. 7A), propylene yield of 15.7% (FIG. 7B), propylene selectivity of 16% (FIG. 7C), and propylene to ethylene molar ratio of 0.71 (FIG. 7D).

The zeolite catalyst prepared in Example 1 exhibited n-heptane conversion ratio of 99.5% (FIG. 7A), propylene yield of 30.1% (FIG. 7B), propylene selectivity of 30.2% (FIG. 7C), and propylene to ethylene molar ratio of 6.4 (FIG. 7D).

The Fe-modified zeolite catalyst prepared in Comparative Example 2-1 exhibited n-heptane conversion ratio of 100% (FIG. 7A), propylene yield of 21.2% (FIG. 7B), propylene selectivity of 21.2% (FIG. 7C), and propylene to ethylene molar ratio of 1.6 (FIG. 7D).

Apparently, the propylene yield achieved by the Al-modified zeolite catalyst prepared in Example 1 was substantially higher than those achieved by the unmodified and Fe-modified zeolite catalysts prepared in Comparative Examples 1-1 and 2-1, respectively, under the same reaction conditions. By combining these results and the Brønsted to Lewis acid ratios determined by Py-IR characterization, it was found that as in the case of the calcination at 550° C., the ratio of the Lewis acid sites in the zeolite catalyst prepared in Example 1 (calcination at 650° C.) was also increased, thereby facilitating the formation of propylene.

Reaction Example 3

The zeolite catalysts prepared in Comparative Examples 3-1 and 3-2 were each used in catalytic cracking of n-heptane. 0.2 g of the zeolite catalyst was mixed with 2 g of SiC fillter and then charged into a fixed bed reactor tube. The mixture was heated to 550° C. at a heating rate of 5° C/min. n-heptane was pumped into the reactor tube at a rate of 0.05 mL/h. Nitrogen gas was introduced thereinto at a rate of 15 mL/min. The preheating temperature was controlled at 300° C. and the reaction was controlled at 550° C. The products were analyzed by GC.

FIG. 8A-D shows comparisons of (a) conversion rates of n-heptane, (b) yields of propylene, (c) selectivities of ethylene and propylene, and (d) $n_{propylene}/n_{ethylene}$ ratios, achieved by the zeolite catalysts prepared in Examples 1 and 5 and in Comparative Examples 3-1 and 3-2.

FIG. 8A-D illustrates whether the calcination process directly affected the catalytic activities of the Al-modified zeolite catalyst to the cracking of n-heptane. As shown in this figure, for the zeolite catalysts prepared in Example 1 (with calcination) and Comparative Example 3-1 (without calcination), the n-heptane conversion rate decreased from 38.5% achieved by the former to 23% achieved by the latter, and the propylene yield decreased from 13.5% achieved by the former to 6.59% achieved by the latter; and for the zeolite catalysts prepared in Example 5 (with calcination) and Comparative Example 3-2 (without calcination), the n-heptane conversion rate decreased from 43.2% achieved by the former to 22% achieved by the latter, and the propylene yield decreased from 16.5% achieved by the former to 3.83% achieved by the latter. Apparently, the calcination was vital to increase the propylene yield.

The conditions for the hydrothermal crystallization, calcination, ion exchange, and impregnation in an Al-containing solution were varied in Examples 1-5 and the zeolite catalysts according to the present disclosure were obtained. Reaction Example 1 was provided to show that these zeolite catalysts can be effectively used in catalytic cracking of n-heptane to produce propylene. The results show that both the yield and the selectivity of propylene were substantially increased and the propylene to ethylene molar ratio was 6 or higher.

What is claimed is:

1. A method for preparing a zeolite catalyst for catalytic cracking of hydrocarbons to produce propylene, the method comprising steps of:
   (1) mixing a silicon source, a templating agent, an aluminium source, and a solvent to form a zeolite precursor solution, which is then subjected to hydrothermal crystallization, washing, drying, and calcination to obtain a zeolite precursor;
   (2) ion-exchanging the zeolite precursor obtained in the step (1) with ammonium ions, followed by drying and calcination; and
   (3) loading aluminum onto the ion-exchanged zeolite precursor obtained in the step (2), as a carrier, via incipient-wetness impregnation by using an aluminium-containing solution, followed by drying and calcination.

2. The method of claim 1, wherein, the templating agent comprises quaternary ammonium surfactants; wherein, the aluminium source comprises one or more of organoaluminum compounds, pseudo boehmite, alumina gel, and organic and inorganic acid salts containing aluminium as well as complexes and hydrates thereof; and wherein the silicon source comprises one or more of silica gel, fumed silica, inorganic silicates, organic silicates, white carbon black, and silicic acid.

3. The method of claim 1, wherein, the zeolite precursor solution obtained in the step (1) contains $SiO_2$, the templating agent, $Al_2O_3$, and $H_2O$ at a molar ratio of 100:(30-60):(0-4):(2000-6000).

4. The method of claim 1, wherein, in the step (1), the hydrothermal crystallization is carried out at a temperature of from 130 to 170° C. for a period of time of from 2 to 15 days, and the calcination is carried out in air atmosphere at a temperature of from 300 to 650° C. for a period of time of from 4 to 12 hours.

5. The method of claim 2, wherein, in the step (1), the hydrothermal crystallization is carried out at a temperature of from 130 to 170° C. for a period of time of from 2 to 15 days, and the calcination is carried out in air atmosphere at a temperature of from 300 to 650° C. for a period of time of from 4 to 12 hours.

6. The method of claim 3, wherein, in the step (1), the hydrothermal crystallization is carried out at a temperature of from 130 to 17020 C. for a period of time of from 2 to 15 days, and the calcination is carried out in air atmosphere at a temperature of from 300 to 650° C. for a period of time of from 4 to 12 hours.

7. The method of claim 1, wherein, in the step (2), the ion-exchange is carried out at a temperature of from 20 to 120° C. for a period of time of from 2 to 48 hours, and the calcination is carried out at a temperature of from 300 to 650° C. for a period of time of from 4 to 12 hours.

8. The method of claim 1, wherein, the aluminum contained in the aluminium-containing solution used in the step (3) is provided by an aluminum source which comprises one or more of $Al(NO_3)_3$, $Al_2(SO_4)_3$, $AlCl_3$, and $Al(OCH(CH_3)_2)_3$, and are present in the solution at a concentration of from 0.1 to 10% by weight; wherein, the incipient-wetness impregnation is carried out at a temperature of from 20 to 120° C. for a period of time of from 6 to 48 hours; and wherein, the calcination in the step (3) is carried out at a temperature of from 300 to 650° C. for a period of time of from 4 to 12 hours.

9. A zeolite catalyst for catalytic cracking of hydrocarbons to produce propylene prepared by the method according to claim 1.

10. The zeolite catalyst of claim 9, wherein, the templating agent comprises quaternary ammonium surfactants; wherein, the aluminium source comprises one or more of organoaluminum compounds, pseudo boehmite, alumina gel, and organic and inorganic acid salts containing aluminium as well as complexes and hydrates thereof; and wherein the silicon source comprises one or more of silica gel, fumed silica, inorganic silicates, organic silicates, white carbon black, and silicic acid.

11. The zeolite catalyst of claim 9, wherein, the zeolite precursor solution obtained in the step (1) contains $SiO_2$, the templating agent, $Al_2O_3$, and $H_2O$ at a molar ratio of 100:(30-60):(0-4):(2000-6000).

12. The zeolite catalyst of claim 9, wherein, in the step (1), the hydrothermal crystallization is carried out at a temperature of from 130 to 170° C. for a period of time of from 2 to 15 days, and the calcination is carried out in air atmosphere at a temperature of from 300 to 650° C. for a period of time of from 4 to 12 hours.

13. The zeolite catalyst of claim 10, wherein, in the step (1), the hydrothermal crystallization is carried out at a temperature of from 130 to 17020 C. for a period of time of from 2 to 15 days, and the calcination is carried out in air atmosphere at a temperature of from 300 to 650° C. for a period of time of from 4 to 12 hours.

14. The zeolite catalyst of claim 11, wherein, in the step (1), the hydrothermal crystallization is carried out at a temperature of from 130 to 170° C. for a period of time of from 2 to 15 days, and the calcination is carried out in air atmosphere at a temperature of from 300 to 650° C. for a period of time of from 4 to 12 hours.

15. The zeolite catalyst of claim 9, wherein, in the step (2), the ion-exchange is carried out at a temperature of from 20 to 120° C. for a period of time of from 2 to 48 hours, and the calcination is carried out at a temperature of from 300 to 650° C. for a period of time of from 4 to 12 hours.

16. The zeolite catalyst of claim 9, wherein, the aluminum contained in the aluminium-containing solution used in the step (3) is provided by an aluminum source which comprises one or more of $Al(NO_3)_3$, $Al_2(SO_4)_3$, $AlCl_3$, and $Al(OCH(CH_3)_2)_3$, and are present in the solution at a concentration of from 0.1 to 10% by weight; wherein, the incipient-wetness impregnation is carried out at a temperature of from 20 to 120° C. for a period of time of from 6 to 48 hours; and wherein, the calcination in the step (3) is carried out at a temperature of from 300 to 650° C. for a period of time of from 4 to 12 hours.

17. The zeolite catalyst of claim 9, having an MFI structure and an average particle size of from 200 to 500 nm and having a Brønsted to Lewis acid ratio of from 0.1 to 1.

18. The zeolite catalyst of claim 10, having an MFI structure and an average particle size of from 200 to 500 nm and having a Brønsted to Lewis acid ratio of from 0.1 to 1.

19. A catalytic cracking process for producing propylene from hydrocarbons by using the zeolite catalyst according to claim 9 as a catalyst.

20. The catalytic cracking process according to claim 19, the zeolite catalyst has an MFI structure and an average particle size of from 200 to 500 nm and has a Brønsted to Lewis acid ratio of from 0.1 to 1.

* * * * *

UNITED STATES PATENT AND TRADEMARK OFFICE
CERTIFICATE OF CORRECTION

PATENT NO.       : 11,717,813 B2
APPLICATION NO.  : 17/890891
DATED            : August 8, 2023
INVENTOR(S)      : Yajie Tian et al.

It is certified that error appears in the above-identified patent and that said Letters Patent is hereby corrected as shown below:

On the Title Page

Item (73) Assignee:
"(73) Assignee: Henan University, Kaipeng (CN)" should read: --(73) Assignee: Henan University, Kaifeng, (CN)--.

Item (30) Foreign Application Priority Data, insert:
--(30) Foreign Application Priority Data
Oct. 15, 2021 (CN).................202111202171.9--.

In the Claims

Column 16, Claim 6, Line 36:
"17020 C." should read: --170 C.--.

Column 6, Claim 8, Line 48:
"Alcl$_3$," should read: --AlCl$_3$,--.

Column 17, Claim 13, Line 13:
"17020 C." should read: --170 C.--.

Signed and Sealed this
Nineteenth Day of November, 2024

Katherine Kelly Vidal
*Director of the United States Patent and Trademark Office*